US009885060B2

(12) United States Patent
Dennig et al.

(10) Patent No.: US 9,885,060 B2
(45) Date of Patent: Feb. 6, 2018

(54) ALKENE PRODUCTION

(71) Applicants: Alexander Dennig, Graz (AT); Kurt Faber, Graz (AT); Melanie Hall, Graz (AT); Thomas Haas, Muenster (DE); Thomas Buelter, Duisburg (DE); Stefan Gilch, Duelmen (DE); Anja Thiessenhusen, Muenster (DE)

(72) Inventors: Alexander Dennig, Graz (AT); Kurt Faber, Graz (AT); Melanie Hall, Graz (AT); Thomas Haas, Muenster (DE); Thomas Buelter, Duisburg (DE); Stefan Gilch, Duelmen (DE); Anja Thiessenhusen, Muenster (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/053,626

(22) Filed: Feb. 25, 2016

(65) Prior Publication Data
US 2016/0326549 A1 Nov. 10, 2016

(30) Foreign Application Priority Data
Feb. 26, 2015 (EP) .................................... 15156699

(51) Int. Cl.
| | | |
|---|---|---|
| C12N 1/20 | (2006.01) | |
| C12P 5/00 | (2006.01) | |
| C12N 9/04 | (2006.01) | |
| C12N 9/08 | (2006.01) | |
| C12P 5/02 | (2006.01) | |
| C12N 9/02 | (2006.01) | |

(52) U.S. Cl.
CPC .............. *C12P 5/00* (2013.01); *C12N 9/0006* (2013.01); *C12N 9/0065* (2013.01); *C12N 9/0095* (2013.01); *C12P 5/026* (2013.01); *C12Y 111/02004* (2013.01); *C12Y 118/01005* (2015.07)

(58) Field of Classification Search
CPC ...................... C12Y 118/01005; C12N 9/0095
USPC ...................................................... 435/252.3
See application file for complete search history.

(56) References Cited

U.S. PATENT DOCUMENTS

| | | | |
|---|---|---|---|
| 8,378,127 | B2 | 2/2013 | Dingerdissen et al. |
| 8,703,451 | B2 | 4/2014 | Haas et al. |
| 8,809,576 | B2 | 8/2014 | Schraven et al. |
| 8,911,982 | B2 | 12/2014 | Schaffer et al. |
| 8,999,684 | B2 | 4/2015 | Poetter et al. |
| 9,005,928 | B2 | 4/2015 | Schaffer et al. |
| 9,012,227 | B2 | 4/2015 | Karau et al. |
| 9,085,787 | B2 | 7/2015 | Schaffer et al. |
| 9,102,968 | B2 | 8/2015 | Schaffer et al. |
| 2011/0118433 | A1 | 5/2011 | Poetter et al. |
| 2011/0171702 | A1 | 7/2011 | Reinecke et al. |
| 2011/0196180 | A1 | 8/2011 | Alibhai et al. |
| 2011/0251399 | A1 | 10/2011 | Dingerdissen et al. |
| 2012/0253088 | A1 | 10/2012 | Alibhai et al. |
| 2013/0052700 | A1 | 2/2013 | Poetter et al. |
| 2013/0330795 | A1 | 12/2013 | Leys et al. |
| 2014/0120587 | A1 | 5/2014 | Haas et al. |
| 2014/0186905 | A1 | 7/2014 | Schaffer et al. |
| 2014/0206057 | A1 | 7/2014 | Alcasabas et al. |
| 2014/0256904 | A1 | 9/2014 | Schaffer et al. |
| 2015/0044744 | A1 | 2/2015 | Pfeffer et al. |
| 2015/0056658 | A1 | 2/2015 | Schaffer et al. |
| 2015/0111254 | A1 | 4/2015 | Hennemann et al. |
| 2015/0140617 | A1 | 5/2015 | Poetter et al. |
| 2015/0218600 | A1 | 8/2015 | Haas et al. |
| 2015/0247151 | A1 | 9/2015 | Schaffer et al. |
| 2015/0267231 | A1 | 9/2015 | Haas et al. |
| 2015/0275245 | A1 | 10/2015 | Haas et al. |
| 2015/0284747 | A1 | 10/2015 | Schiemann et al. |
| 2015/0299741 | A1 | 10/2015 | Engel et al. |
| 2015/0353963 | A1 | 12/2015 | Haas et al. |

FOREIGN PATENT DOCUMENTS

| | | |
|---|---|---|
| WO | WO 2009/085278 A1 | 7/2009 |
| WO | WO 2013/186215 A1 | 12/2013 |
| WO | WO 2014/102201 A1 | 7/2014 |

OTHER PUBLICATIONS

Extended European Search Report dated Aug. 12, 2015 in Patent Application 15156699.9.
Yi Liu, et al., "Hydrogen Peroxide-Independent Production of a-alkenes by OleTJE P450 Fatty Acid Decarboxylase" Biotechnology for biofuels, vol. 7, No. 1, XP021179059, Feb. 24, 2014, pp. 1-12.
James Belcher, et al., "Structure and Biochemical Properties of the Alkene Producing Cytochrome P450 OleTJE (CYP152L1) from the *Jeotgalicoccus* sp. 8456 Bacterium" The Journal of Biological Chemistry, vol. 289, No. 10, XP055206214, Mar. 7, 2014, pp. 6535-6550 and Cover page.
Mathew A. Rude, et al., "Terminal Olefin (1-Alkene) Biosynthesis by a Novel P450 Fatty Acid Decarboxylase from *Jeotgalicoccus* Species" Applied Environmental Microbiology, vol. 77, No. 5, XP055107226, Jan. 7, 2011, 36 Pages.

(Continued)

*Primary Examiner* — Tekchand Saidha
(74) *Attorney, Agent, or Firm* — Oblon, McClelland, Maier & Neustadt, L.L.P.

(57) ABSTRACT

The present invention provides a microbial cell capable of producing at least one terminal alkene from at least one short chain fatty acid, wherein the cell is genetically modified to comprise at least a first genetic mutation that increases the expression relative to the wild type cell of an enzyme ($E_1$) selected from the CYP152 peroxygenase family, and at least a second genetic mutation that increases the expression relative to the wild type cell of at least one NAD(P)+ oxidoreductase ($E_2$) and the corresponding mediator protein, wherein the short chain fatty acid is a C4-C10 fatty acid.

20 Claims, 11 Drawing Sheets

(56) References Cited

OTHER PUBLICATIONS

Takashi Fujishiro, et al., "Crystal Structure of $H_2O_2$-Dependent Cytochrome P450SPα with Its Bound Fatty Acid Substrate: Insight Into the Regioselective Hydroxylation of Fatty Acids at the α Position" The Journal of Biological Chemistry, vol. 286, No. 34, XP055206228, Aug. 26, 2011, pp. 29941-29950 and Cover page.

Anett Schallmey, et al., "Characterization of Cytochrome P450 Monooxygenase CYP154H1 from the Thermophilic Soil Bacterium *Thermobifida fusca*" Applied Microbiology and Biotechnology, vol. 89, No. 5, XP019880853, Nov. 6, 2010, pp. 1475-1485.

Alexander Dennig, et al., "Oxidative Decarboxylation of Short-Chain Fatty Acids to 1-Alkenes" Angewandte Chemie International Edition, vol. 54, No. 30, XP055206218, 2015, pp. 8819-8822.

US 9,885,060 B2

ALKENE PRODUCTION

BACKGROUND OF THE INVENTION

Field of the Invention

The present invention relates to a cell and/or a biotechnological method that is capable of producing at least one alkene from at least one fatty acid. In particular, the alkene is at least one terminal alkene produced from a short chain fatty acid.

Discussion of the Background

Various methods have been studied to transform biomass into valuable chemical compounds that can be used as sustainable alternatives to petroleum. Petroleum, the main source for chemical building blocks and transportation fuel, is being continuously depleted, and the prices perpetually fluctuating. Accordingly, there is a need to find an alternative energy source. One such energy source is alkenes.

For example, short and medium chain α-olefins serve as not only biofuels but also as polymer building blocks. In particular, alkenes may be used broadly for making lubricants, polymers and detergents.

Fatty acids are the preferred starting materials for production of alkenes as they contain carbon at low oxidation state. Also, fatty acids can usually be obtained in large quantities at low prices from natural resources, such as fats.

The current methods used in the production of alkenes from fatty acids are chemical in nature where α-olefins are formed from saturated unbranched fatty acids ($\geq C_{11}$). These methods usually require expensive and/or toxic metal-based catalysts and high temperatures ($>130°$ C.).

In 2011, Rude et al. reported the first direct enzymatic decarboxylation of unbranched saturated long chain $C_{18}$- and $C_{16}$-fatty acids (stearic and palmitic acids) into α-olefins employing the P450 monooxygenase OleT. The catalyst was operated via its peroxide shunt using $H_2O_2$ as oxidant which circumvented the need for natural redox partners. Belcher, J., et al., 2014 then disclosed the crystal structure of OleT and the substrate scope was expanded to $C_{12}$-fatty acid (lauric acid). However, the use of $H_2O_2$ as an oxidant has several safety concerns and not only destroys the machinery it may be found in but is also unstable. The need to constantly add $H_2O_2$ into the reaction mixture also increases the cost of the reaction and is inconvenient. Accordingly, the biotechnical methods available are inefficient and incapable of producing high yields at low costs. There is thus a need in the art for an improved biotechnological method of producing alkenes from renewable resources.

SUMMARY OF THE INVENTION

The cell according to any aspect of the present invention solves the problems mentioned above by providing a biotechnological means of producing alkenes from short chain fatty acids. In particular, the cell according to any aspect of the present invention provides a novel enzyme cascade for the biocatalytic synthesis of terminal alkenes by oxidative decarboxylation of short chain unbranched, saturated fatty acids with at least a chain length of $C_4$-$C_{10}$ wherein the cell does not require $H_2O_2$. The novel enzyme cascade comprises a decarboxylation reaction which is $H_2O_2$-independent and may be catalyzed by at least one P450 monooxygenase. In particular, the cell comprises expresses an enzyme, for example OleT, which may be capable of optimising a biocatalytic system to produce at least one alkene from a short chain fatty acid using decarboxylation reactions.

DETAILED DESCRIPTION OF THE INVENTION

In one aspect of the present invention, there is provided a microbial cell capable of producing at least one terminal alkene from at least one short chain fatty acid, wherein the cell is genetically modified to comprise
at least a first genetic mutation that increases the expression relative to the wild type cell of an enzyme ($E_1$) selected from the CYP152 peroxygenase family, and
least a second genetic mutation that increases the expression relative to the wild type cell of at least one NAD(P)+ oxidoreductase ($E_2$) and the corresponding mediator protein,
wherein the short chain fatty acid is a $C_4$-$C_{10}$ fatty acid.

In contrast to the usual chemo-catalytic routes which are usually used to produce alkenes, the method according to any aspect of the present invention may use whole cells or isolated enzymes. This allows for the method to be carried out under mild reaction conditions, thereby enabling sustainable processes with minimal waste emission. This is an unexpected result as prior art (Fujishiro T., 2007 and Matsunaga I., 2002) reported that P450 reductase systems such as ferredoxin and ferredoxin reductase did not support the activity of P450$_{BSβ}$ and P450$_{SPα}$.

Further, the cell according to any aspect of the present invention allows for large scale production of alkenes from the short chain fatty acids used as substrates. This can be seen in the examples where a substrate concentration of 10 mM was used to produce the corresponding alkene. This was an unexpected result as the currently available methods of alkene production show the conversion of maximum of substrates such as steric acid to the respective alkene.

According to another aspect of the present invention, there is provided a method of producing at least one terminal alkene from at least one short chain fatty acid.

The method according to any aspect of the present invention has further advantages such as it uses $O_2$ as an oxidant, that makes the process more efficient than the methods known in the art which use $H_2O$ as an oxident; the method allows for electron transfer from renewable resources and the method according to any aspect of the present invention also results in significantly high production of alkenes.

According to a further aspect of the present invention, there is provided nose of the cell according to any aspect of the present invention to produce at least one terminal alkene.

The cell according to any aspect of the present invention may directly use free fatty acids instead of fatty acid thioesters as substrates, which may be advantageous for metabolic engineering because fatty acids may be more abundant. Further, their abundance and composition can be more readily manipulated in cells that have been commonly used as microbial cell factories, for example, E. coli.

Thus, the cell according to any aspect of the present invention with the P450 fatty acid decarboxylative machinery may hold great potential to be engineered into a biological terminal alkene-producing system. Further, the cell according to any aspect of the present invention, provides an optimised biocatalytic system for decarboxylation reactions (>100 mg $L^{-1}$) and extends the substrate scope to short chain fatty acids.

Terminal alkenes may also be known as terminal olefins which refer to unsaturated hydrocarbons containing at least one carbon-carbon double bond the end of the carbon chain. This C—C double bond may be at the beginning (α) or at the end (γ) of the hydrocarbon chain. The simplest acyclic alkenes, with only one double bond and no other functional groups may have the general formula $C_nH_{2n}$. In another example, the terminal alkenes may also comprise other functional groups. The terminal alkene according to any aspect of the present invention may comprise the same number of carbon atoms as the number of carbon atoms as the substrate short chain fatty acid. For example, if the substrate is butyric acid, the terminal alkene formed may be propene. Similarly, if the substrate is valeric acid/pentanoic acid, the terminal alkene formed may be butene; if the substrate is caproic acid/hexanoic acid, the terminal alkene formed may be pentene; if the substrate is enanthic acid/heptanoic acid, the terminal alkene formed may be hexene; if the substrate is caprylic acid/octanoic acid, the terminal alkene formed may be heptene; if the substrate is pelargonic acid/nonanoic acid the terminal alkene formed may be octene; if the substrate is capric acid/decanoic acid the terminal alkene formed may be nonene and the like. In one example, the alkenes produced such as propene and/or 1-butene from the respective fatty acids may be measured using novel means shown in the examples.

The term "short chain fatty acid" used in the present invention refers to a sub-group of fatty acids with aliphatic tails of less than 10 carbons. The fatty acid may be a saturated, unsaturated, branched or unbranched fatty acid. In particular, the short chain fatty acid used according to any aspect of the present invention may be selected from the group consisting of propionic acid, butyric acid/butanoic acid, valeric acid/pentanoic acid, caproic acid/hexanoic acid, enanthic acid/heptanoic acid, caprylic acid/octanoic acid, pelargonic acid/nonanoic acid, capric acid/decanoic acid and the like. More in particular, the short chain fatty acid used according to any aspect of the present invention may be a $C_2$-$C_{22}$ fatty acid. Even more in particular, the fatty acid may be a $C_4$-$C_{10}$ fatty acid. In one example, the fatty acid may be selected from the group consisting of acetic acid, propionic acid, isobutyric acid (2-methylpropanoic acid), butyric acid, isovaleric acid (3-methylbutanoic acid), valeric acid (pentanoic acid), and the like.

The cell according to any aspect of the present invention may refer to a wide range of microbial cells. In particular, the cell may be a prokaryotic or a lower eukaryotic cell selected from the group consisting of *Pseudomonas*, *Corynebacterium*, *Bacillus* and *Escherichia*. In one example, the cell may be *Escherichia coli*. In another example, the cell may be a lower eukaryote, such as a fungus from the group comprising *Saccharomyces*, *Candida*, *Pichia*, *Schizosaccharomyces* and *Yarrowia*, particularly, *Saccharomyces cerevisiae*. The cell may be an isolated cell, in other words a pure culture of a single strain, or may comprise a mixture of at least two strains. Biotechnologically relevant cells are commercially available, for example from the American. Type Culture Collection (ATCC) or the German Collection of Microorganisms and Cell Cultures (DSMZ), Particles for keeping and modifying cells are available from the prior art, for example Sambrook/Fritsch/Maniatis (1989).

The phrase "wild type" as used herein in conjunction with a cell or microorganism may denote a cell with a genome make-up that is in a form as seen naturally in the wild. The term may be applicable for both the whole cell and for individual genes. The term "wild type" therefore does not include such cells or such genes where the gene sequences have been altered at least partially by man using recombinant methods.

Any of the enzymes used according to any aspect of the present invention, may be an isolated enzyme. In particular, the enzymes used according to any aspect of the present invention may be used in an active state and in the presence of all cofactors, substrates, auxiliary and/or activating polypeptides or factors essential for its activity. The term "isolated", as used herein, means that the enzyme of interest is enriched compared to the cell in which it occurs naturally. The enzyme may be enriched by SDS polyacrylamide electrophoresis and/or activity assays. For example, the enzyme of interest may constitute more than 5, 10, 20, 50, 75, 80, 85, 90, 95 or 99 percent of all the polypeptides present in the preparation as judged by visual inspection of a polyacrylamide gel following staining with Coomassie blue dye.

The cell and/or enzyme used according to any aspect of the present invention may be recombinant. The term "recombinant" as used herein, refers to a molecule or is encoded by such a molecule, particularly a polypeptide or nucleic acid that, as such, does not occur naturally but is the result of genetic engineering or refers to a cell that comprises a recombinant molecule. For example, a nucleic acid molecule is recombinant if it comprises a promoter functionally linked to a sequence encoding a catalytically active polypeptide and the promoter has been engineered such that the catalytically active polypeptide is overexpressed relative to the level of the polypeptide in the corresponding wild type cell that comprises the original unaltered nucleic acid molecule.

Whether or not a nucleic acid molecule, polypeptide, more specifically an enzyme used according to any aspect of the present invention, is recombinant or not has not necessarily implications for the level of its expression. However, in one example one or more recombinant nucleic acid molecules, polypeptides or enzymes used according to any aspect of the present invention may be overexpressed. The term "overexpressed", as used herein, means that the respective polypeptide encoded or expressed is expressed at a level higher or at higher activity than would normally be found in the cell under identical conditions in the absence of genetic modifications carried out to increase the expression, for example in the respective wild type cell. The person skilled in the art is familiar with numerous ways to bring about overexpression. For example, the nucleic acid molecule to be overexpressed or encoding the polypeptide or enzyme to be overexpressed may be placed under the control of a strong inducible promoter such as the lac promoter. The state of the art describes standard plasmids that may be used for this purpose, for example the pET system of vectors exemplified by pET-3a (commercially available from Novagen). Whether or not a nucleic acid or polypeptide is overexpressed may be determined by way of quantitative PCR reaction in the case of a nucleic acid molecule, SDS polyacrylamide electrophoreses, Western blotting or comparative activity assays in the case of a polypeptide. Genetic modifications may be directed to transcriptional, translational, and/or post-translational modifications that result in a change of enzyme activity and/or selectivity under selected and/or identified culture conditions. Thus, in various examples of the present invention, to function more efficiently, a microorganism may comprise one or more gene deletions. Gene deletions may be accomplished by mutational gene deletion approaches, and/or starting with a mutant strain having reduced or no expression of one or more of these enzymes, and/or other methods known to those skilled in the art.

The enzyme ($E_1$) selected from the CYP152 peroxygenase family used according to any aspect of the present invention may be part of the superfamily cytochrome P450 enzymes (CYPs) (Malca et al., 2011). Typically, P450 enzymes employ one or more redox partner proteins to transfer two electrons from NAD(P)H to the heme iron reactive center for dioxygen activation, and then insert one atom of $O_2$ into their substrates. The enzymes within the family of CYP152 peroxygenases have been identified to exclusively use $H_2O_2$ as the sole electron and oxygen donors. However, in the cell according to any aspect of the present invention, NAD(P)+ oxidoreductase ($E_2$) and the corresponding mediator protein may be used as the source of electron and oxygen donors. This is advantageous as in a large scale production of low-cost terminal alkenes, the use of large amounts of peroxide is cost prohibitive, and high concentration of $H_2O_2$ can quickly deactivate biocatalysts. Accordingly, the use of NAD(P)+ oxidoreductase ($E_2$) and the corresponding mediator protein as a source of electrons provides a more cost-effective microbial production of terminal alkenes. This may be further explained in Liu et al., 2014.

In particular, enzyme $E_1$ may be selected from the group consisting of $CYP_{SP\alpha}$ ($E_{1a}$), $CYP_{BSB}$ ($E_{1b}$)) (EC 1.11.2.4) and OleT ($E_{1c}$). More in particular, the enzyme $E_1$ may be OleT ($E_{1c}$) or a variant thereof. In one example, enzyme $E_1$ may comprise the sequence of ADW41779.1. In one example, the enzyme $E_1$ may have 50, 55, 60, 65, 70, 75, 80, 85, 90, 95, 98, 100% sequence identity to SEQ NO:1.

A skilled person would be capable of identifying the possible sequences of OleT that may be used to carry other the process of forming at least one terminal alkene from at least one fatty acid. In one example, the skilled person may use the disclosure in Liu et al, 2014, Rude M. A. 2011, Schallmey, A., 2011, Fukada H., 1994, Belcher J., 2014 and the like to determine the structure and means of introducing OleT ($E_{1c}$) into a suitable cell and determining the expression of the enzyme in the cell. OleT (as compared to other $H_2O_2$-dependent enzymatic reactions) may lead to an artificial electron transfer system to higher yield.

The cell according to any aspect of the present invention may comprises a second genetic mutation that increases the expression relative to the wild type cell of at least one enzyme, the NAD(P)+ oxidoreductase ($E_2$) and the corresponding mediator protein. These enzymes belong to a family of oxidoreductases that oxidise the mediator protein and accept two electrons. In particular, NAD(P)+ oxidoreductases use iron-sulphur proteins as electron donors and $NAD^-$ or $NADP^+$ as electron acceptors. Hannermann et al. discloses a list of various classes of redox-mediators that may be used asenzyme $E_2$ according to any aspect of the present invention. In one example, artificial/"chemical" redox mediators could transfer electrons either from reductases or electrical sources to the heme iron cluster.

More in particular, the NAD(P)+ oxidoreductase (EC 1.18.1.5) and the corresponding protein may be selected from the group consisting of:

(a) ferredoxin reductase ($E_{2a}$) and ferredoxin; or
(b) putidaredoxin reductase ($E_{2b}$) and putidaredoxin (Schallmey, A., 2011).

In particular, $E_2$ may be CamA and the mediator protein may be CamB. $E_2$ may comprise 50, 55, 60, 65, 70, 75, 80, 85, 90, 95, 98, 100% sequence identity to SEQ ID: NO:2 and/or the mediator protein may comprise 50, 55, 60, 65, 70, 75, 80, 85, 90, 95, 98, 100% sequence identity to SEQ ID: NO:3.

In one example, in the cell according to any aspect of the present invention $E_2$ may be ferredoxin reductase ($E_{2a}$) where ferredoxin may also be present and $E_{2a}$ may be capable of functionally interacting with $E_1$, In particular, the source of $E_1$ and $E_2$ may be the same or different. In one example, both $E_1$ and $E_2$ may come from the same source, for example from *Alcanivorax borkumensis* SK2 (accession number YP_691921). In this example, $E_{2a}$ and ferredoxin may have accession numbers YP_691923 and YP_691920, respectively.

In another example, in the cell according to any aspect of the present invention $E_2$ may be putidaredoxin reductase ($E_{2b}$) where putidaredoxin may also be present and $E_{2b}$ may be capable of functionally interacting with $E_1$. In one example, $E_{2b}$ may be from the $P450_{cam}$ enzyme system from *Pseudomonas putida*. For putidaredoxin reductase, typically the amount of enzyme employed may be about 100 to 10,000 ca, 1000 to 5000 ca, 2000 to 4000 ca or in particular 3000 ca. The ca is the unit of activity of putidaredoxin reductase in mediating the oxidation of NADI1 by ferricyanide and is defined as 1 μmole of NADH oxidised per mg reductase per minute.

$E_2$ be recombinant protein or a naturally occurring protein which has been purified or isolated. The $E_2$ may have been mutated to improve its performance such as to optimise the speed at which it carries out the electron transfer or its substrate specificity. The amount of reductase employed will depend on the exact nature of what is measured and the particular details of the assay but typically, the reductase will be present at a concentration of from 0 to 1000 μM, 0.001 to 100 μM, 0.01 to 50 μM, 0.1 to 25 μM, and in particular from 1 to 10 μM.

The cell according to any aspect of the present invention further comprises at least a third genetic mutation that increases the expression relative to the wild type cell of at least one enzyme ($E_3$) capable of cofactor regeneration. In particular, $E_3$ may be capable of NAD(P)H regeneration. $E_3$ may be any enzyme that may be capable of NAD(P)H regeneration. In particular, $E_3$ may be a dehydrogenase/oxidoreductase which uses NAD(P) as electron acceptor (EC 1.1.1.X). More in particular, $E_3$ may be any enzyme with KEGG no. EC 1.1.1.X in the Brenda database as of 24 Feb. 2014. For example, $E_3$ may be selected from the group consisting of alcohol dehydrogenase glycerol phosphate dehydrogenase, histidinol dehydrogenase, shikimate dehydrogenase, lactate dehydrogenase, 3-hydroxyaryl-CoA dehydrogenase, malate dehydrogenase, isocitrate dehydrogenase, glucose-6-phosphate dehydrogenase, formate dehydrogenase horse liver alcohol dehydrogenase, glucose dehydrogenase, amino acid dehydrogenase, sorbitol dehydrogenase, 20-β-hydroxysteroid dehydrogenase and formaldehyde dehydrogenase. Even more in particular, enzyme ($E_3$) may be selected from the group consisting of glucose dehydrogenase ($E_{3a}$) (EC 1.1.99.10), phosphite dehydrogenase ($E_{3b}$) (EC 1.20.1.1) and formate dehydrogenase ($E_{3c}$) (EC 1.2.1.43) where glucose, phosphite and formate are used as reducing agents respectively. The presence of enzyme ($E_3$) allows for cofactor regeneration that enables the process of producing alkenes from fatty acids to be self-sustaining. No external energy would thus have to be introduced into the system of producing alkenes. Accordingly, the cell according to any aspect of the present invention may be able to generate at least one alkene from a fatty acid in the presence of at least enzymes $E_1$, $E_2$ and/or $E_3$ without any external energy source needed.

In one example, the glucose dehydrogenase ($E_{3a}$) may be NADP+-specific glucose dehydrogenase. The organism that serves as the source of glucose dehydrogenase ($E_{3a}$) is not subject to limitation, and may be a microorganism or a higher organism, and microorganisms such as bacteria, fungi, and yeast are suitable. For example, a microorganism of the genus *Bacillus*; in particular *Bacillus megaterium*, may be the source. In another example, the source may be a microorganism belonging to the genus *Cryptococcus*, the genus *Gluconobacter*, or the genus *Saccharomyces*. In particular, a microorganism belonging to the genus *Cryptococcus* may be selected, more in particular, the microorganism may be selected from the group consisting of *Cryptococcus albi dus*, *Cryptococcus humicolus*, *Cryptococus terreus*, and *Cryptococcus uniguttulatus*.

In another example, enzyme $E_3$ may be phosphite dehydrogenase ($E_{3b}$) or formate dehydrogenase ($E_{3c}$). The organism that serves as the source of phosphite dehydrogenase ($E_{3b}$) or formate dehydrogenase ($E_{3c}$) may not be subject to limitation, and may be a microorganism or a higher organism, and microorganisms such as bacteria, fungi, and yeast are suitable.

In one example, the cell according to any aspect of the present invention has increased expression relative to a wild type cell of enzymes $E_{1c}$, $E_{2a}$ and $E_{3A}$. In another example, the cell according to any aspect of the present invention has increased expression relative to a wild type cell of $E_{1c}$, $E_{2a}$ and $E_{3b}$; $E_{1c}$, $E_{2a}$ and $E_{3c}$; $E_{1c}$, $E_{2b}$ and $E_{3a}$; $E_{1c}$, $E_{2b}$ and $E_{3b}$; or $E_{1c}$, $E_{2b}$ and $E_{3c}$.

The teachings of the present invention may not only be carried out using biological macromolecules having the exact amino acid or nucleic acid sequences referred to in this application explicitly, for example by name or, accession number, or implicitly, but also using variants of such sequences. The term "variant", as used herein, comprises amino acid or nucleic acid sequences, respectively, that are at least 70, 75, 80, 85, 90, 92, 94, 95, 96, 97, 98 or 99% identical to the reference amino acid or nucleic acid sequence, wherein preferably amino acids other than those essential for the function, for example the catalytic activity of a protein, or the fold or structure of a molecule are deleted, substituted or replaced by insertions or essential amino acids are replaced in a conservative manner to the effect that the biological activity of the reference sequence or a molecule derived therefrom is preserved. The state of the art comprises algorithms that may be used to align two given nucleic acid or amino acid sequences and to calculate the degree of identity, see Arthur Lesk (2008), Thompson et al., 1994, and Katoh et al., 2005. The term "variant" is used synonymously and interchangeably with the term "homologue". Such variants may be prepared by introducing deletions, insertions or substitutions in amino acid or nucleic acid sequences as well as fusions comprising such macromolecules or variants thereof. In one example, the term "variant", with regard to amino acid sequence, comprises, in addition to the above sequence identity, amino acid sequences that comprise one or more conservative amino acid changes with respect to the respective reference or wild type sequence or comprises nucleic acid sequences encoding amino acid sequences that comprise one or more conservative amino acid changes. In one example, the term "variant" of an amino acid sequence or nucleic acid sequence comprises, in addition to the above degree of sequence identity, any active portion and/or fragment of the amino acid sequence or nucleic acid sequence, respectively, or any nucleic acid sequence encoding an active portion and/or fragment of an amino acid sequence. The term "active portion", as used herein, refers to an amino acid sequence or a nucleic acid sequence, which is less than the full length amino acid sequence or codes for less than the full length amino acid sequence, respectively, wherein the amino acid sequence or the amino acid sequence encoded, respectively, retains at least some of its essential biological activity. For example an active portion and/or fragment of a protease may be capable of hydrolysing peptide bonds in polypeptides. The phrase "retains at least some of its essential biological activity", as used herein, means that the amino acid sequence in question has a biological activity exceeding and distinct from the background activity and the kinetic parameters characterising said activity, more specifically $k_{cat}$ and $K_M$, are preferably within 3, 2, or 1 order of magnitude of the values displayed by the reference molecule with respect to a specific substrate. Similarly, the term "variant" of a nucleic acid comprises nucleic acids the complementary strand of which hybridises, preferably under stringent conditions, to the reference or wild type nucleic acid. A skilled person would be able to easily determine the enzymes $E_1$, $E_2$ and/or $E_3$ that will be capable of making alkenes from fatty acids according to any aspect of the present invention.

An illustration of the difference in the reaction that takes place in the cell according to any aspect of the present invention in the presence of $H_2O_2$ and the absence of $H_2O_2$ (i.e. in the presence of enzyme and the mediator protein instead) is shown in Scheme 1. In particular, in scheme 1 (A), an enzymatic redox-cascade for decarboxylation of saturated fatty acids to terminal-olefins is shown. The electrons are shown to be transferred from a hydride donor (e.g. glucose, formate or phosphite) via CamAB to OleT that catalyzes the oxidative decarboxylation of fatty acids at the expense of atmospheric $O_2$ to terminal olefins with chain lengths ranging from $C_3$-$C_{21}$. Side products detected are shown in brackets. In scheme 1 (B), the same reaction in the presence of $H_2O_2$ is shown.

Scheme 1: Oxidative decarboxylation of unbranched saturated fatty acids with OleT.

A

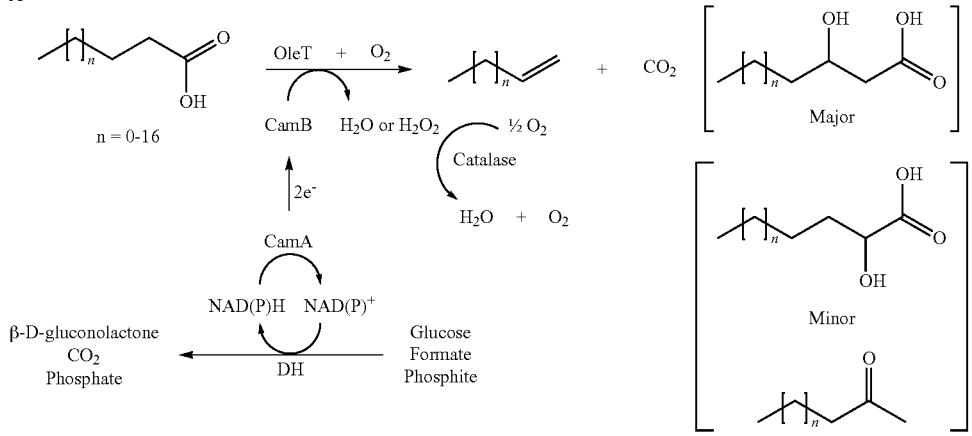

B

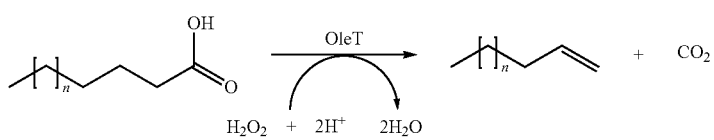

Stringency of hybridisation reactions is readily determinable by one ordinary skilled in the art, and generally is an empirical calculation dependent on probe length, washing temperature and salt concentration. In general, longer probes require higher temperatures for proper annealing, while shorter probes need lower temperatures. Hybridisation generally depends on the ability of denatured DNA to reanneal to complementary strands when present in an environment below their inciting temperature. The higher the degree of desired homology between the probe and hybridisable sequence, the higher the relative temperature which may be used. As a result it follows that higher relative temperatures would tend to make the reaction conditions more stringent, while lower temperature less so. For additional details and explanation of stringency of hybridisation reactions, see F. M. Ausubel (1995), The person skilled in the art may follow the instructions given in the manual "The DIG System Users Guide for Filter Hybridization", Boehringer Mannheim GmbH, Mannheim, Germany, 1993 and in Liebl et al., 1991 on how to identify DNA sequences by means of hybridisation. In one example, stringent conditions are applied for any hybridisation, i.e. hybridisation occurs only if the probe is 70% or more identical to the target sequence. Probes having a lower degree of identity with respect to the target sequence may hybridise, but such hybrids are unstable and will be removed in a washing step under stringent conditions, for example by lowering the concentration of salt to 2×SSC or, optionally and subsequently, to 0.5×SSC, while the temperature is, in order of increasing preference, approximately 50° C.-68° C., approximately 52° C.-68° C., approximately 54° C.-68° C., approximately 56° C.-68° C. approximately 58° C.-68° C., approximately 60° C.-68° C., approximately 62° C.-68° C., approximately 64° C.-68° C., approximately 66° C.-68° C., in a particularly preferred embodiment, the temperature is approximately 64° C.-68° C. or approximately 66° C.-68° C. It is possible to adjust the concentration of salt to 0.2×SSC or even 0.1×SSC, Polynucleotide fragments having a degree of identity with respect to the reference or wild type sequence of at least 70, 80, 90, 91, 92, 93, 94, 95, 96, 97, 98, 99% may be isolated. The term "homologue" of a nucleic acid sequence, as used herein, refers to any nucleic acid sequence that encodes the same amino acid sequence as the reference nucleic acid sequence, in line with the degeneracy of the genetic code.

A skilled person would be capable of easily measuring the activity of each of the enzymes $E_1$, $F_2$ and $E_3$. For example, to determine if the expression of $E_1$ is increased in a cell, a skilled person may use the assay disclosed in Liu et at, 2014, Rude M. A, 2011, Schallmey, A., 2011, and the like. For example, to determine if the expression of $E_2$ is increased in a cell, a skilled person may use the assay disclosed in Scheps, D, 2011, Roome et al., Schallmey et al. and the like. The expression of $E_3$ in a cell, whether it is increased or decreased, may be measured using the assay disclosed at least in Cartel et al. where formate dehydrogenase activity determination (via NAD(P)+ reduction is determined as change in absorbance at 340 nm. A skilled person would easily be able to identify other well-known methods in the art that may be used for measuring the expression of the enzymes used in the cell of the present invention.

The cell according to any aspect of the present invention may have reduced capacity of fatty acid degradation by beta-oxidation relative to the wild type cell. In particular, the reduced fatty acid degradation activity compared to the wild type cell may be a result of decreased expression relative to the wild type cell of at least one enzyme selected from the group consisting of acyl-CoA dehydrogenase (FadE) ($E_6$) (EC:1.3.99.-), enoyl-CoA hydratase (FadB) ($E_a$) (EC 4.2.1.17), (R)-3-hydroxyacyl-CoA dehydrogenase (FadB) ($E_8$) (EC 1.1.1.35) and 3-ketoacyl-CoA thiolase (FadA) ($E_9$) (EC:2.3.1.16).

The term "having a reduced fatty acid degradation capacity", as used herein, means that the respective cell degrades fatty acids, in particular those taken up from the environment, at a lower rate than a comparable cell or wild type cell having normal fatty acid degradation capacity would under identical conditions. In one example, the fatty acid degradation of such a cell is lower on account of deletion, inhibition or inactivation of at least one gene encoding an enzyme involved in the β-oxidation pathway. In one example, at least one enzyme involved in the β-oxidation pathway has lost, in order of increasing preference, 5, 10, 20, 40, 50, 75, 90 or 99% activity relative to the activity of the same enzyme under comparable conditions in the respective wild type microorganism. The person skilled in the art may be familiar with various techniques that may be used to delete a gene encoding an enzyme or reduce the activity of such an enzyme in a cell, for example by exposition of cells to radioactivity followed by accumulation or screening of the resulting mutants, site-directed introduction of point mutations or knock out of a chromosomally integrated gene encoding for an active enzyme, as described in Sambrook/Fritsch/Maniatis (1989). In addition, the transcriptional repressor FadR may be over expressed to the effect that expression of enzymes involved in the β-oxidation pathway is repressed (Fujita, Y., et al, 2007). The phrase "deletion of a gene", as used herein, means that the nucleic acid sequence encoding said gene is modified such that the expression of active polypeptide encoded by said gene is reduced. For example, the gene may be deleted by removing in-frame a part of the sequence comprising the sequence encoding for the catalytic active centre of the polypeptide. Alternatively, the ribosome binding site may be altered such that the ribosomes no longer translate the corresponding RNA, It would be within the routine skills of the person skilled in the art to measure the activity of enzymes expressed by living cells using standard essays as described in enzymology text books, for example Cornish-Bowden, 1995.

Degradation of fatty acids is accomplished by a sequence of enzymatically catalysed reactions. First of all, fatty acids are taken up and translocated across the cell membrane via a transport/acyl-activation mechanism involving at least one outer membrane protein and one inner membrane-associated protein which has fatty acid-CoA ligase activity, referred to in the case of $E.$ $coli$ as FadL and FadD/FadK, respectively. Inside the cell, the fatty acid to be degraded is subjected to enzymes catalysing other reactions of the β-oxidation pathway. The first intracellular step involves the conversion of acyl-CoA enoyl-CoA through acyl-CoA dehydrogenase, the latter referred to as FadE in the case of $E.$ $coli$. The activity of an acyl-CoA dehydrogenase may be assayed as described in the state of art, for example by monitoring the concentration of NADH spectrophotometrically at 340 nm in 100 mM MOPS, pH 7.4, 0.2 mM Enoyl-CoA, 0.4 mM NAD$^+$. The resulting enoyl-CoA is converted to 3-ketoacyl-CoA via 3-hydroxylacyl-CoA through hydration and oxidation, catalysed by enoyl-CoA hydratase/(R)-3-hydroxyacyl-CoA dehydrogenase, referred to as FadB and FadJ in $E.$ $coli$. Enoyl-CoA hydratase/3-hydroxyacyl-CoA dehydrogenase activity, more specifically formation of the product NADH may be assayed spectrophotometrically as described in the state of the art, for example as outlined for FadE. Finally, 3-ketoacyl-CoA thiolase, FadA and FadI in $E.$ $coli$, catalyses the cleavage of 3-ketoacyl-CoA, to give acetyl-CoA and the input acyl-CoA shortened by two carbon atoms. The activity of ketoacyl-CoA thiolase may be assayed as described in the state of the art, for example in Antonenkov, V., et al, 1997.

The phrase "a cell having a reduced fatty acid degradation capacity", as used herein, refers to a cell having a reduced capability of taking up and/or degrading fatty acids, particularly those having at least eight carbon chains. The fatty acid degradation capacity of a cell may be reduced in various ways. In particular, the cell according to any aspect of the present invention has, compared to its wild type, a reduced activity of an enzyme involved in the β-oxidation pathway. The term "enzyme involved in the β-oxidation pathway", as used herein, refers to an enzyme that interacts directly with a fatty acid or a derivative thereof formed as part of the degradation of the fatty acid via the β-oxidation pathway. The β-oxidation pathway comprises a sequence of reactions effecting the conversion of a fatty acid to acetyl-CoA and the CoA ester of the shortened fatty acid. The enzyme involved in the β-oxidation pathway may by recognizing the fatty acid or derivative thereof as a substrate, converts it to a metabolite formed as a part of the β-oxidation pathway. For example, the acyl-CoA dehydrogenase (EC 1.3.99.-) is an enzyme involved in the β-oxidation pathway as it interacts with fatty acid-CoA and converts fatty acid-CoA ester to enoyl-CoA, which is a metabolite formed as part of the β-oxidation. In another example, the tem "enzyme involved in the β-oxidation pathway", as used herein, comprises any polypeptide from the group comprising acyl-CoA dehydrogenase (EC 1.3.99.-), enoyl-CoA hydratase (EC 4.2.1.17), 3-hydroxyacyl-CoA dehydrogenase (EC 1.1.1.35) and 3-keto-acyl-CoA thiolase (EC 2.3.1.16). The acyl-CoA synthetase (EC 6.2.1.1) may catalyse the conversion of a fatty acid to the CoA ester of a fatty acid, i.e. a molecule, wherein the functional group OH of the carboxy group is replaced with S-CoA and introducing the fatty acid into the β-oxidation pathway. For example, the polypeptides FadD and FadK in $E.$ $coli$ (accession number: BAA15609.1 and NP_416216.4, respectively) are acyl-CoA dehydrogenases. In one example, the term "acyl-CoA dehydrogenase", as used herein, may be a polypeptide capable of catalysing the conversion of an acyl-CoA enoyl-CoA, as part of the β-oxidation pathway. For example, the polypeptide FadE in $E.$ $coli$ (accession number: BAA77891.2) may be an acyl-CoA dehydrogenase. The term "enoyl-CoA hydratase", as used herein, also referred to as 3-hydroxyacyl-CoA dehydrogenase, refers to a polypeptide capable of catalysing the conversion of enoyl-CoA to 3-ketoacyl-CoA through hydration and oxidation, as part of the β-oxidation pathway. For example, the polypeptides FadB and FadJ in $E.$ $coli$ (accession numbers: BAE77457.1 and P77399.1, respectively; are enoyl-CoA hydratases. The term "ketoacyl-CoA thiolase", as used herein, may refer to a polypeptide capable of catalysing the cleaving of 3-ketoacyl-CoA, resulting in an acyl-CoA shortened by two carbon atoms and acetyl-CoA, as the final step of the β-oxidation pathway. For example, the polypeptides FadA and FadI in $E.$ $coli$ (accession number: YP_491599.1 and P76503.1, respectively) are ketoacyl-CoA thiolases.

The term "contacting", as used herein, means bringing about direct contact between the amino acid, the fatty acid and/or the cell according to any aspect of the present invention in an aqueous solution. For example, the cell, the amino acid and the fatty acid may not be in different compartments separated by a barrier such as an inorganic membrane. If the amino acid or fatty acid is soluble and may be taken up by the cell or can diffuse across biological membranes, it may simply be added to the cell according to any aspect of the present invention in an aqueous solution. In case it is insufficiently soluble, it may be solved in a suitable organic solvent prior to addition to the aqueous solution. The person skilled in the art is able to prepare aqueous solutions of amino acids or fatty acids having insufficient solubility by adding suitable organic and/or polar solvents. Such solvents may be provided in the form of an organic phase comprising liquid organic solvent. In one example, the organic solvent or phase may be considered liquid when liquid at 25° C. and standard atmospheric pressure. In another example, a fatty acid may be provided in the form of a fatty acid ester such as the respective methyl or ethyl ester. In another example, the compounds and catalysts may be contacted in vitro, i.e. in a more or less enriched or even purified state, or may be contacted in situ, i.e. they are made as part of the metabolism of the cell and subsequently react inside the cell.

The term "an aqueous solution" or "medium" comprises any solution comprising water, mainly water as solvent that may be used to keep the cell according to any aspect of the present invention, at least temporarily, in a metabolically active and/or viable state and comprises, if such is necessary, any additional substrates. The person skilled in the art is familiar with the preparation of numerous aqueous solutions, usually referred to as media that may be used to keep inventive cells, for example LB medium in the case of *E. coli*. It is advantageous to use as an aqueous solution a minimal medium, i.e. a medium of reasonably simple composition that comprises only the minimal set of salts and nutrients indispensable for keeping the cell in a metabolically active and/or viable state, by contrast to complex mediums, to avoid dispensable contamination of the products with unwanted side products. For example, M9 medium may be used as a minimal medium.

According to any aspect of the present invention, the fatty acid is added to an aqueous solution comprising the cell according to any aspect of the present invention. This step may not only comprise temporarily contacting the fatty acid with the solution, but in fact incubating the fatty acid in the presence of the cell sufficiently long to allow for an oxidation reaction and possible further downstream reactions to occur, for example for at least 1, 2, 4, 5, 10 or 20 hours. The temperature chosen must be such that the inventive cells remains catalytically competent and/or metabolically active, for example 10 to 42° C., preferably 30 to 40° C., in particular, 32 to 38° C. in case the cell is an *E. coli* cell.

In one example, the method according to any aspect of the present invention may comprise a further step of adding a "water-immiscible organic solvent" into the mixture of the cell according to any aspect of the present invention and fatty acids either following step (a) or simultaneously with step (a). The person skilled in the art knows numerous water-immiscible organic solvents that may be used according to any aspect of the present invention. In one example, the term "water-immiscible organic solvent", as used herein, refers to a compound comprising at least two carbon atoms and having the tendency to form, in the presence of an aqueous liquid phase, at 25° C., another liquid phase, which is clearly separate from the aqueous phase. The separate phase may be a continuous liquid phase or an emulsion. In on example, the term "water-immiscible", as used herein, refers to the tendency of a liquid compound not to be soluble in the water. In another example, the term "water-immiscible", as used herein, means that a compound designated as such has a pH-value (J Sangster, 1997) the decadic logarithm of which exceeds 0, 0.5, 1 or 2. Examples of water-immiscible organic solvents include, but are not limited to water-immiscible solvents from the group comprising substituted and linear alkanes liquid at room temperature, cycloalkanes, cycloalkenes, aryls, fatty acids, fatty acid esters, alcohols, heterocycloalkanes, heterocycloalkenes and heteroaryls. The water-immiscible organic solvents may comprise more than one organic solvent. In a preferred embodiment, the term "extracting" a product using a "water-immiscible organic solvent", as used herein, means that the aqueous solution comprising the cell according to any aspect of the present invention is contacted with the water-immiscible organic solvent sufficiently long as to allow the product to enter the phase comprising the water-immiscible solvent. Subsequently, the phase comprising the water-immiscible organic solvent may be separated from the aqueous solution, for example by distillation or by decantation.

In one example, the water-immiscible organic solvent may be a fatty acid or an ester thereof, in one example, the fatty acid is represented by the formula $CH_3-(CH_2)_x-COORs$, wherein x is 8, 9, 10, 28 and is more preferably 12 or more than 12, and wherein Rs is H, or alkyl, the latter may be methyl or ethyl. In one example, the water-immiscible organic solvent may be an unsaturated fatty acid, one having a carbon-carbon double bond at position 9 of the carbon chain, or one having 12 carbon atoms or more. In another example, the water-immiscible organic solvent may be oleic acid or hexanoic acid or lauric acid methyl ester. The volume of the water-immiscible organic solvent is such that it is straightforward to separate it from the aqueous solution. In one example, the volume of the water-immiscible organic solvent is 2 to 98, 5 to 95, 10 to 40, or 20 to 30 percent of the total combined volumes of aqueous solution and water-immiscible organic solvent.

In particular, the cofactor of the method according to any aspect of the present invention may be NAD+/NADH. More in particular, the method further comprises a coupled process of cofactor regeneration for regenerating the consumed cofactor NAD(P)+. The coupled cofactor regenerating process also comprises the regeneration of the consumed sacrificial glucose, formate, phosphine or the like.

BRIEF DESCRIPTION OF FIGURES

The inventions are further illustrated by the following figures and non-limiting examples from which further embodiments, aspects and advantages of the present invention may be taken.

Figure 1:
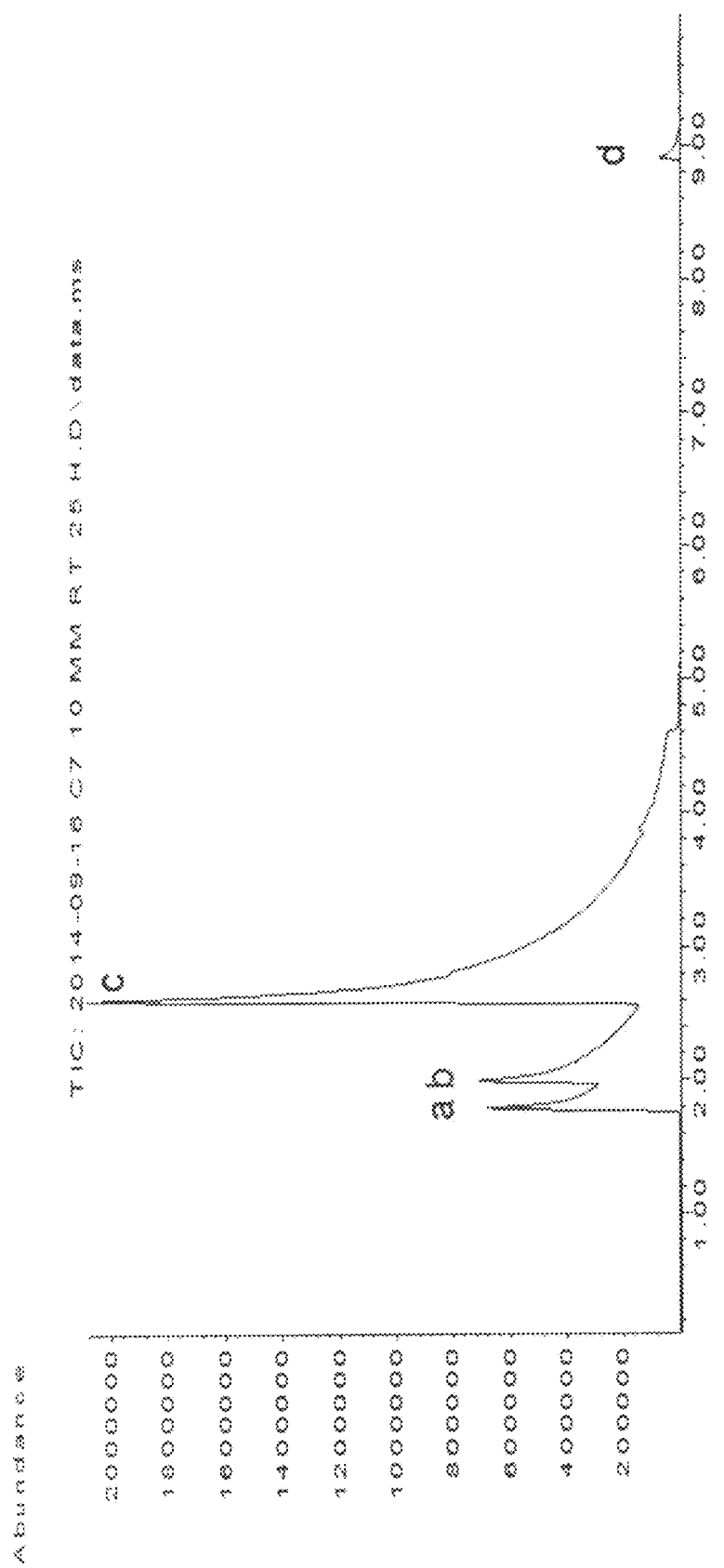
FIG. 1 is a chromatogram obtained from a conversion of heptanoic acid with the OleT-CamABFDH (cascade, a=CO2; b=EtOH; c=1-hexene; d=MIBK (derived from EtOH). Compounds were injected manually from the reaction vessel headspace into a GC-MS chromatograph.

Having generally described this invention, a further understanding can be obtained by reference to certain specific examples which are provided herein for purposes of illustration only, and are not intended to be limiting unless otherwise specified.

EXAMPLES

The foregoing describes preferred embodiments, which, as will be understood by those skilled in the art, may be subject to variations or modifications in design, construction or operation without departing from the scope of the claims. These variations, for instance, are intended to be covered by the scope of the claims.

Example 1

Cloning, Expression and Quantification of OleT

All chemicals were obtained from Sigma Aldrich. Spinach ferredoxin, spinach ferredoxin reductase, catalase from bovine liver, lysozyme, cytochrome c from bovine heart and glucose dehydrogenase (NADPH-dependent, clarify commercial source were obtained from Sigma Aldrich. Formate dehydrogenase (NADH-dependent) was obtained from Evocatal. Phosphite dehydrogenase (PDH) (Dudek, H. M., 2013) was prepared according) a standard protocol, the plasmid was obtained from M. Fraaije (Groningen).

OleT was ordered from Life Technologies as codon-optimized synthetic gene for optimal expression in $E.\ coli$. The synthetic construct was cloned via restriction/ligation (NdeI and XhoI) into the pET28a expression vector downstream (pET28a-OleT) of an N-terminal His$_6$-tag prior to chemical transformation into $E.\ coli$ Snuffle® T7 strain (New England Biolabs). Successful cloning was verified by colony PCR, restriction analysis and sequencing. Cells containing pET28a-OleT were grown overnight (140 rpm, 37° C.) as pre-culture in lysogeny broth (LB) media supplemented with 50 kanamycin. Expression of OleT was achieved by transferring 2 mL of pre-culture into 200 mL terrific broth (TB) media according to a published protocol (Nazor, J, 2009). Efficient expression of OleT was achieved after 20 h incubation at 25° C. and 140 rpm shaking. Cells were separated from expression media by centrifugation and pellets were stored for 24 h at −20° C., Frozen cell pellets were resuspended in purification buffer (KPi; 0.1 M; pH 7.0; 20% glycerol, 0.3 M KCl; 50 mM imidazol). Lysozyme was added (1 mg mL$^{-1}$) followed by incubation at 37° C. for 1 h. Cells were finally disrupted by sonication (1 min, 30% amplitude) using an ultra sonicator. Cell debris was pelleted by centrifugation and cell free lysates were pressed through a 0.45 µm filter to remove residual particles. Filtered cell free lysate was loaded onto a His-Trap column connected to a Biorad FPLC pumping system with UV-detector. OleT was purified according to the protocol of Matsunaga et al., 2001 but using 400 mM (instead of 200 mM) imidazol for the final elution step. During dialysis of purified OleT with the reported dialysis buffer (KPi, 0.1 M, pH 7.0, 20% glycerol), large amounts of the protein precipitated (active protein concentrations of only 1 to 2 µM OleT retained). In order to remove residual imidazole and to prevent precipitation, dialysis was performed against phosphate buffer (KPi, 0.1 M, pH 7.0, 20% glycerol) containing 300 mM KCl. The protein lysates were filled in in a dialysis tubing cellulose membrane (14 kDa cut off, Sigma Aldrich, Steinheim, Germany a dialysis bag and dialyzed three times against 300 ml of dialysis buffer (3×12 h) at 4° C. and continuous stirring. No visible precipitation occurred during the dialysis procedure and active P450 concentrations of >10 µM were commonly obtained. Concentrations of active P450 protein in cell free lysates or purified OleT were determined by recording CO difference spectra.

Cloning, Expression and Quantification of CamAB System

Expression of CamA and CamB (CamAB) was done according to a published protocol employing the reported plasmid construct and $E.\ coli$ host (Schallmey, A., 2011).

Product Extraction, Derivatization of Fatty and Hydroxy Acids

Enzymatic reactions (1 mL scale) were quenched by addition of 100 µL 5 N Extraction of substrate and products was performed with 500 µL EtOAc containing 0.1% 1-decanol as internal standard. The organic phase was dried over anhydrous $Na_2SO_4$. Derivatization of carboxylic acids (fatty acids and hydroxy acids) to the corresponding methyl esters was achieved by mixing the organic phase with MeOH (2.5:1.5 v/v) followed by supplementation of 5 to 15 µL of 2 M TMSCHN$_2$ (trimethylsilyldiazomethane in diethyl ether). The mixture was incubated for 30 min, 25° C. and 750 rpm before injection into GC-FID or GC-MS, Extraction and derivatization of products and substrates from conversion of short chain FAs (C12-C9) was performed using the same protocol but all steps were performed on ice to prevent undesired loss of volatile products.

Preparation of Samples for Headspace GC-MS Analysis

Products from FA substrates with chain lengths ranging from C22 to C10 were separated on a HP5 column (Programm) and detected by GC-FID or GC-MS. Extracted products from conversion of nonanoic acid (I-octene as product) were separated on a DB1702 column (Programm) and detected by GC-FID. Authentic standards of substrates and terminal olefins were treated as described above and were used as references for identification and preparation of calibration curves. Detection of volatile short chain terminal olefins (1-butene/1-propene [ongoing] to 1-heptene) was accomplished by manual injection from vial headspaces into GC-MS, in order to prevent loss of products, the vials containing the reaction mixtures were sealed with a PTFE septum. After conversion the closed vial was heated for 10 min at 80° C., together with a 10 ml syringe (TYPE). From the headspace 2 to 9 µl volumes were injected splitless into a GC-MS chromatograph and analytes were separated on a HP5 column (Programm). Calibration curves for 1-pentene, 1-hexene and 1-heptene were prepared in the same way at 4° C. and using 5% DMF as cosolvent.

Example 2

Conversion of FAs with the CamAB-OleT Redox Cascade and $O_2$ as Oxidant

An optimized purification protocol allowed the improved production of OleT in active form (10-20 µM from 400 mL culture broth), avoiding protein precipitation during dialysis (ESI). Bacterial CamAB (putidaredoxin; class 1) was used as an electron transfer system (Koga H., 1989 and Roome P. W., 1983) (Scheme 1). Initial experiments confirmed that OleT can accept electrons from CamAB allowing the decarboxylation of stearic acid with $O_2$ as sole oxidant, whereas control reactions did not lead to any product formation (Table 1). Further, lower CamAB concentration was found to be optimum for higher conversions. No formation of $H_2O_2$ (formed via reduction of $O_2$) could be detected by using the highly sensitive HRP/ABTS assay (Sigma Aldrich) according to manufacturer's protocol after full oxidation of 1 mM NADH, further indicating a direct electron transfer from CamAB to OleT and ruling out potential inactivation of OleT by $H_2O_2$.

TABLE 1

Catalytic characterization of OleT using either $O_2$/CamAB or $H_2O_2$ as oxidant for decarboxylation of stearic and palmitic acid.

| Entry | Oxidant/ Electron Source | Reaction Time [min] | α-Olefin [μM] | TOF [h$^{-1}$] | Coupling [%] | TON [—] |
|---|---|---|---|---|---|---|
| | | Stearic Acid | | | | |
| 1 | 200 μM NADPH + $O_2$ | 60 | 53 ± 5 | 53 | 25 | 53 |
| 2 | 1 mM NADPH + $O_2$ | 150 | 118 ± 23 | 47 | 11 | 118 |
| 3 | 200 μM NADH + $O_2$ | 6 | 15 ± 1 | 150 | 7 | 15 |
| 4 | 1 mM NADH + $O_2$ | 60 | 20 ± 2 | 20 | 2 | 20 |
| 5 | 200 μM $H_2O_2$ | 60 | 170 ± 7 | 170 | 85 | 170 |
| 6 | 1 mM $H_2O_2$* | 150 | 53 ± 15 | 21 | 5 | 53 |
| | | Palmitic Acid | | | | |
| 7 | 200 μM NADPH + $O_2$ | 60 | 21 | 21 | 10 | 21 |
| 8 | 1 mM NADPH + $O_2$ | 150 | 33 | 13 | 3 | 33 |
| 9 | 200 μM NADH + $O_2$ | 6 | 6 | 60 | 3 | 60 |
| 10 | 1 mM NADH + $O_2$ | 60 | 9 | 9 | 1 | 9 |
| 11 | 200 μM $H_2O_2$ | 60 | 65 | 65 | 33 | 65 |
| 12 | 1 mM $H_2O_2$* | 150 | 73 | 29 | 7 | 29 |
| 13 | Control reactions | 150 | 0 | 0 | 0 | 0 |

Reaction conditions: 1 μM OleT, 0.05 U ml$^{-1}$ CamAB, 1200 U ml$^{-1}$ catalase, 1 mM substrate, 2.5% EtOH, KPi buffer (pH 7.5, 0.1M).
Conversions were performed in plastic cuvettes at room temperature and without agitation.
Reactions with $H_2O_2$ as oxidant contained only OleT, substrate, buffer and hydrogen peroxide.
*Strong precipitation observed.
[1]One of the following components was left out of the reaction: OleT, $H_2O_2$, CamAB, NAD(P)H or substrate.

Example 3

Conversion of FAs with the CamAB-OleT Redox Cascade and NAD(P)H Regeneration System The use of a glucose dehydrogenase (GDH)-based system provided a substantial increase in conversion (36% conversion with 1 mM stearic acid) and TIN (up to 389 with 10 mM stearic acid), with comparable conversions of both stearic and palmitic acid. After 24 h reaction time, product concentrations of 1.16 mM (0.27 g L-1) 1-heptadecene and 1 mM (0.21 g L-1) 1-pentadecene were obtained but could not be further enhanced. The inhibitory effect of gluconic acid, formed as side-produce from NAD(P)H regeneration by GDH and glucose, was therefore investigated and already a concentration of 10 mM was found to reduce OleT productivity significantly (28% reduction). Alternative systems based on phosphite dehydrogenase (PDH; NADPH-dependent) (Dudek, 2013 and Vrtis J. M., 2002) and formate dehydrogenase (EDIT; NADH-dependent)-based (Busto E., 2014) proved to be more efficient: 2.6 mM (0.62 g L-1) and 3.1 mM (0.75 g L-1) 1-heptadecene, respectively, were obtained from 5 mM stearic acid (52% and 62% conversion, respectively), yielding the highest TIN values so far (1739 and 2096, respectively) by using the above mentioned regeneration systems. Compared to a previously published whole cell reaction system, this FDH-driven system allows 6 times higher product titer and a 21 times higher volumetric productivity with 42.5 mg L-1 h-1 of α-olefin after 8 h reaction time vs: 98 mg L-1 in 48 h) (Table 2).

TABLE 2

Decarboxylation of stearic acid by OleT employing various redox partner systems using $O_2$ as oxidant.

| Electron Source | Redoxpartners | OleT | α-Olefin [μM] | Product [g L$^{-1}$] | TTN [—] |
|---|---|---|---|---|---|
| Glucose | GDH-CamAB | Purified [1.5 μM] | 1020 ± 63 | 0.24 | 680 |
| Phosphite | PDH-CamAB | Purified [1.5 μM] | 2609 ± 256 | 0.62 | 1739 |
| Formate | FDH-CamAB | Purified [1.5 μM] | 3144 ± 121 | 0.75 | 2096 |
| Formate [8 h] | FDH-CamAB | Purified [3 μM] | 1419 | 0.34 | 473 |
| Formate | FDH-CamAB-Fdr/Fdx[a] | Cell free lysate [3 μM] | 1565 ± 20 | 0.37 | 522 |
| Formate | FDH-(Fdr/Fdx)[a] | Cell free lysate [3 μM] | 452 ± 52 | 0.1 | 151 |

Reaction conditions: 0.05 U ml$^{-1}$ CamAB, 1200 U ml$^{-1}$ catalase, 12 U ml$^{-1}$ GDH or 2 U ml$^{-1}$ GDH or 0.2 U ml$^{-1}$ PDH, 100 mM D-glucose or 100 mM ammonium formate or 100 mM sodium phosphite, 5 mM stearic acid, 2.5% EtOH, KPi buffer (pH 7.5, 0.1M) and 200 μM NAD(P)H. Reactions were performed at 1 ml scale at room temperature and 170 rpm shaking for 24 h in closed glass vials.
[a]Fdr/Fdx is naturally present in E. coli and allows transfer of electrons from NAD(P)H to OleT.
[b]Reactions contained 53 mg of freeze-dried lysates of cells expressing OleT.

Example 4

Decarboxylation Fatty Acids (FAs) Employing the PDH-CamAB-OleT Redox-Cascade The substrate scope of OleT was further investigated by varying the FA chain length from C3 to C22. In addition to the standard setup at RT, the reaction was also investigated at 4° C. to prevent loss of highly volatile short chain α-olefins, which resulted in surprisingly high activity levels (Table 3). For the first time, short FAs could be decarboxylated to the corresponding olefins, covering the whole spectrum from C11 down to C4. Interestingly, the conversion of short chain FAs (<C10) was recognized by a strong 'gasoline odor' released from reaction tubes. Due to the high volatility of short chain olefins, product work up was done at 4° C. Yields were strongly dependent on the reaction temperature and the substrate chain length, with a major drop in reactivity at RT below C18 (maximum product concentration 2.45 mM from 5 mM stearic acid), while C12 appears the best substrate at 4° C. (2.53 mM product from 5 mM lauric acid). Head-space analysis by GC-MS from reactions with short chain FAs (C8-C5) confirmed the formation of the respective α-olefins, allowing the first biotechnological access to 1-heptene, 1-hexene and 1-pentene and 1-butene with OleT.

TABLE 3

Decarboxylation of FAs employing the FDH-CamAB-OleT redox-cascade.

| FA | Temp. [° C.] | α-Olefin [μM] | Conversion [%] | Selectivity [% GC-area] α-Olefin | α-OH | β-OH | n-Alkanone |
|---|---|---|---|---|---|---|---|
| C22 | 25 | n.q. | 16* | >99 | n.d. | Traces | n.d. |
|  | 4 |  |  | 93 | n.d. | 7 | n.d. |
| C20 | 25 | n.q. | 3* | >99 | n.d. | Traces | n.d. |
|  | 4 |  |  | >99 | n.d. | n.d. | n.d. |
| C18 | 25 | 3886 | 39 | 86 | 2 | 8 | 6 |
|  | 4 | 2451 | 25 | 93 | <1 | 5 | 5 |
| C16 | 25 | 1111 | 11 | 72 | 3 | 23 | 8 |
|  | 4 | 2059 | 21 | 80 | <1 | 14 | 6 |
| C14 | 25 | 552 | 6 | 62 | 4 | 31 | n.d. |
|  | 4 | 1247 | 12 | 87 | n.d. | 13 | n.d. |
| C12 | 25 | 273 | 3 | n.d. | n.d. | n.d. | n.d. |
|  | 4 | 3260 | 33 | 73 | n.d. | 30 | n.d. |
| C11 | 25 | n.d. | 0 | n.d. | n.d. | n.d. | n.d. |
|  | 4 | 191 | 2 | >99 | n.d. | n.d. | n.d. |
| C10 | 25 | 44 | 0.4 | >99 | n.d. | Traces | n.d. |
|  | 4 | 71 | 0.7 | >99 | n.d. | n.d. | n.d. |
| C9 | 25 | 1829 | 18 | 53 | 17 | 30 | n.d. |
|  | 4 | 1347 | 13 | on-going | on-going | on-going |  |
| C8 | 25 | 364 | 3.6 | n.i. | n.i. | n.i. | n.i. |
|  | 4 | 141 | 1.4 |  |  |  |  |
| C7 | 25 | 1298 | 13 | n.i. | n.i. | n.i. | n.i. |
|  | 4 | 946 | 9.5 |  |  |  |  |
| C6 | 25 | 1170 | 12 | n.i. | n.i. | n.i. | n.i. |
|  | 4 | 772 | 7.7 |  |  |  |  |
| C5 | 25 | 834 | 8.3 | n.i. | n.i. | n.i. | n.i. |
| C4 | 25 | 504 | 5 | n.i. | n.i. | n.i. | n.i. |

Reaction conditions: Conversion of substrates C22-C14 was performed using 3 μM OleT, 6 μM OleT for substrates C12-C3.
All reactions mixtures contained 0.05 U ml−1 CamAB, 1200 U ml−1 catalase, 2 U ml−1 FDH, 100 mM ammonium formate, 5% EtOH, 10 mM substrate, KPi buffer (pH 7.5, 0.1M) and 200 μM NADH.
Conversion of substrates C8, C7 and C6 were done in presence of 5% DMSO as cosolvent.
Detection and quantification of short-chain terminal olefins was achieved using manual headspace GC-MS injection.
All conversions were performed at 1 ml scale and 170 rpm shaking in closed glass vials (RT samples/24 h) or stirring (4° C. samples/72 h).
*relative to conversions with C18/only GC-areas.
n.i. = not investigated.

Example 5

Identification and Quantification of 1-Hexene Produced from Heptanoic Acid by OleT Conversion of heptanoic acid was carried out as described in Example 4 using the OleTCamAB-FDH reaction cascade. Decarboxylation of heptanoic acid proceeded reliably as shown in FIG. 1.

Figure 2:
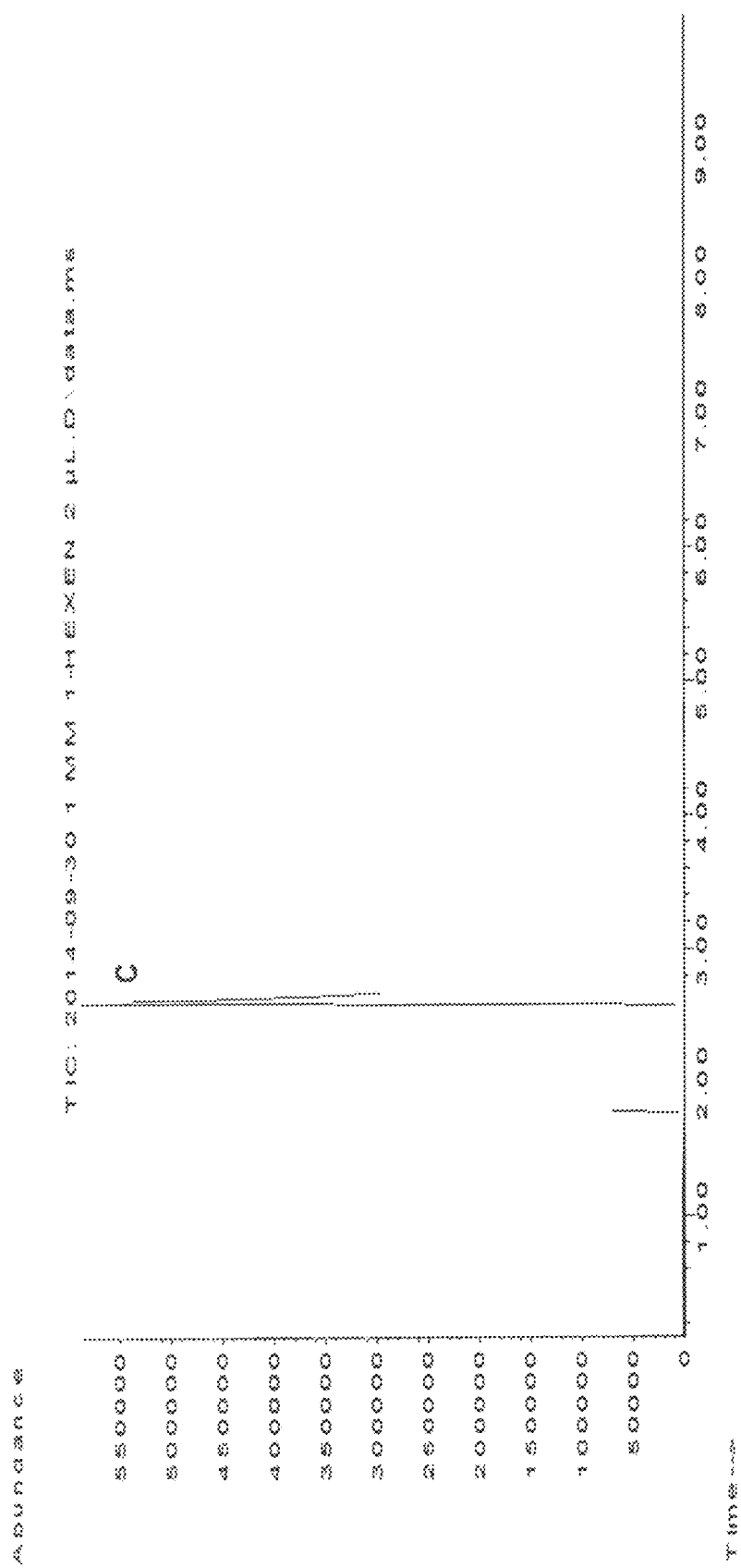
FIG. 2 is a chromatogram after manual headspace GC-MS injection of an analytical standard of 1-hexene.
Figure 3:
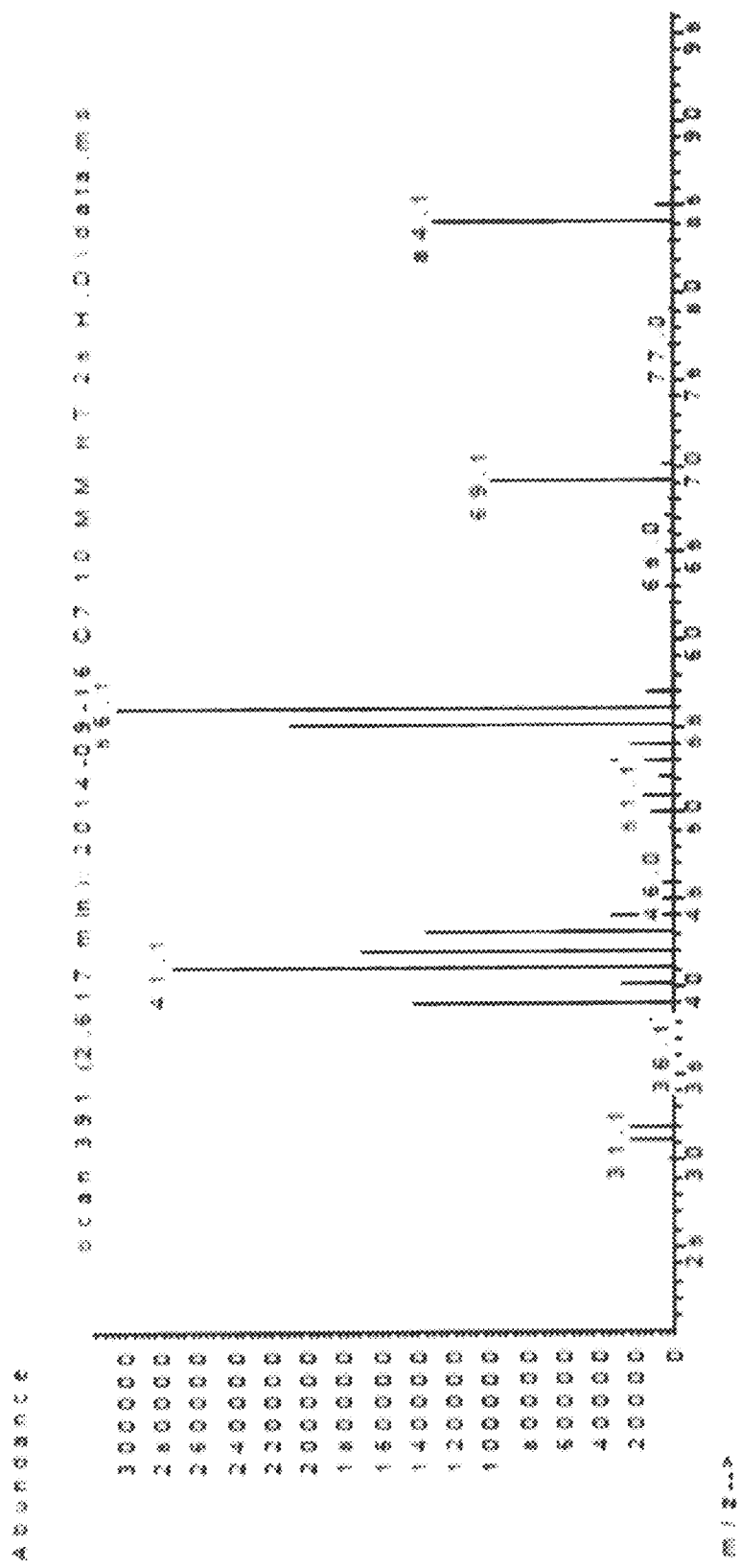
FIG. 3 is a graph of the GC-MS spectrum for peak c in FIG. 1 corresponding to 1-hexene (84.1 g/mol).
Figure 4:
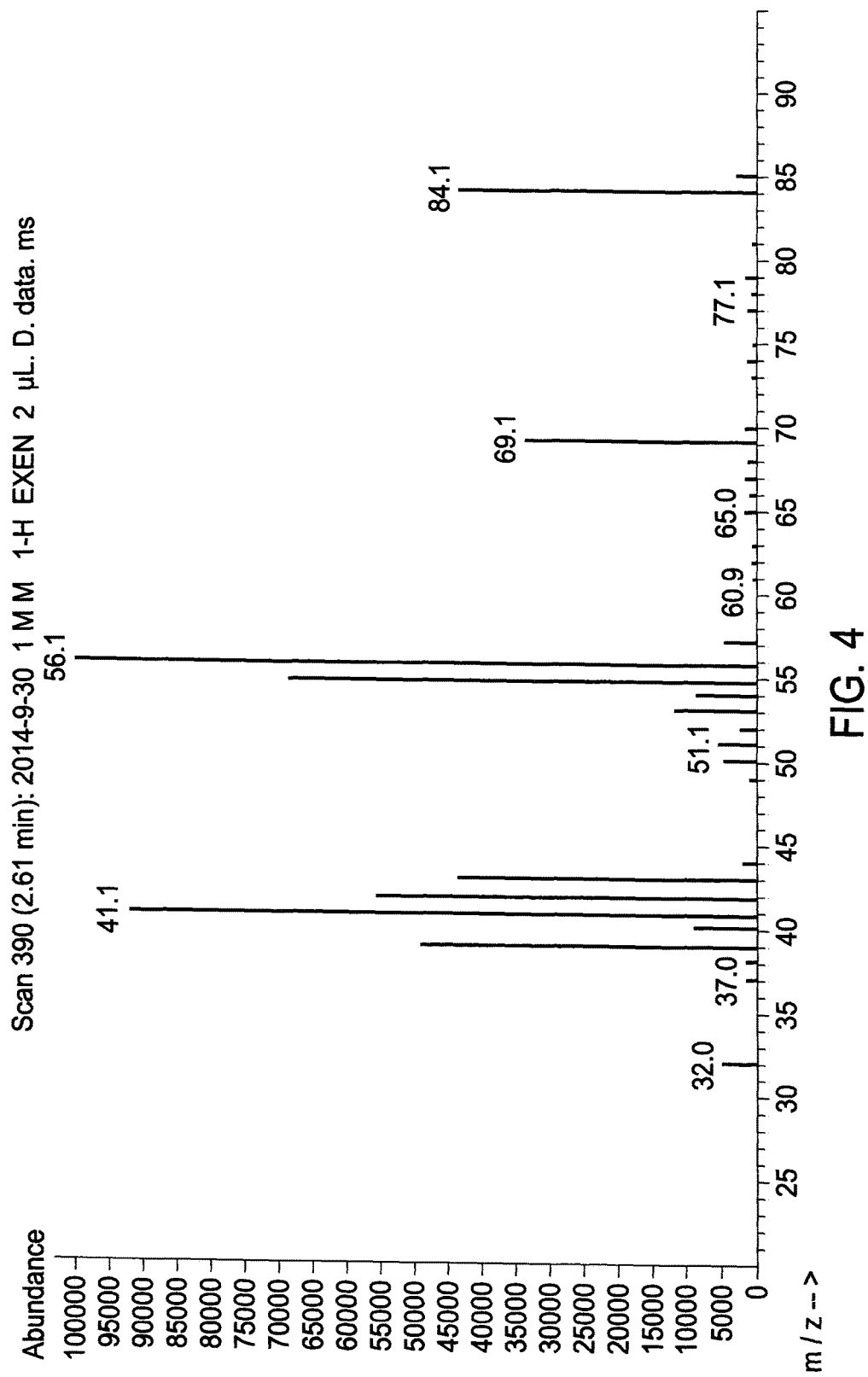
FIG. 4 is a graph of the GC-MS spectrum for peak c in FIG. 2 corresponding to the analytical standard of 1-hexene (84.1 g/mol).

An analytical standard of 1-hexene was used to confirm formation of the target product. The analytical standard eluted at the same retention time (2.617 min; FIGS. 1 and 2, peak c) and displayed the identical m/z pattern as the reaction product formed by OleT (FIGS. 3 and 4).

Figure 5:
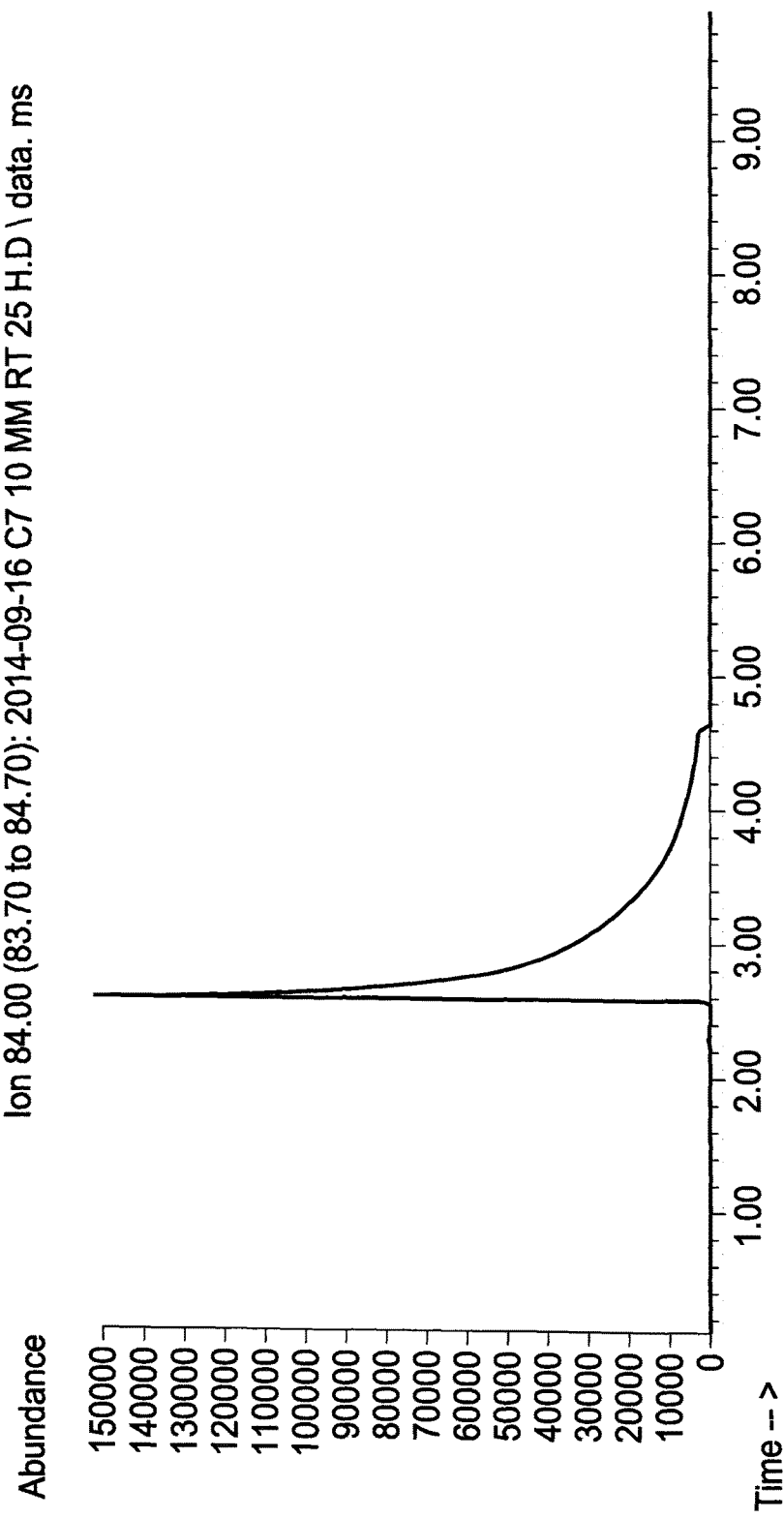
FIG. 5 is a chromatogram obtained after ion extraction of ion 84 from conversion of heptanoic acid with the OleT-CamAB-FDH cascade.
Figure 6:
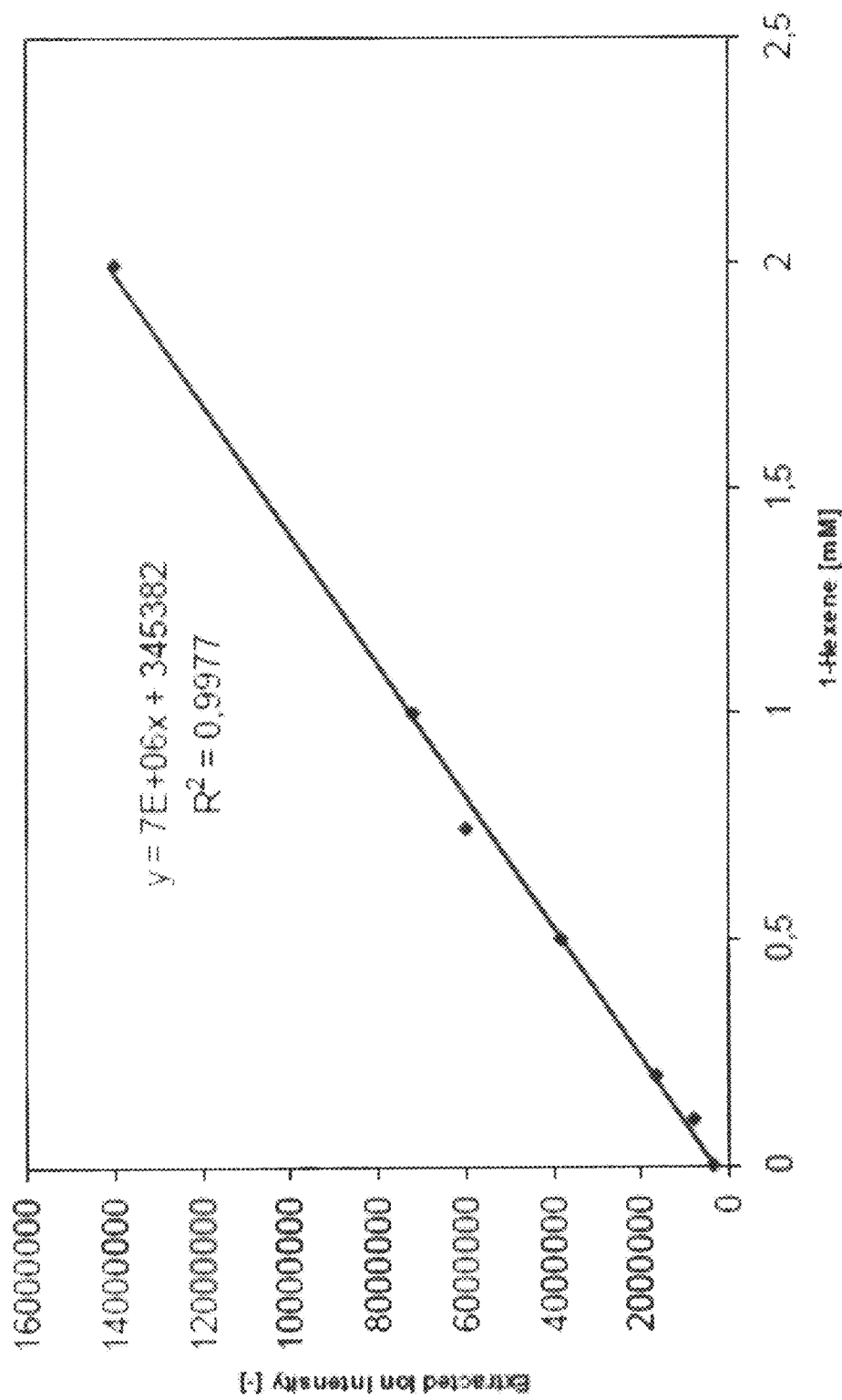
FIG. 6 is a calibration curve for manual headspace GC-MS injection of 1-hexene using peak area of extracted ion 84.

Calibration curves for 1-hexene were prepared accordingly ranging from 0.05 to 2 mM. Due to a strong overlap of 1-hexene with the peak areas of $CO_2$ and EtOH (FIG. 1, peaks a, b and c) the ion extraction mode of the GC-MS to generate reliable calibration curves was used. For 1-hexene the characteristic ion 84 for quantification as shown in FIG. 5 was used. Neither $CO_2$ nor EtOH interfered with the product peak area. This can be seen comparing FIGS. 1 and 5 which allow reliable and linear quantification of 1-hexene (FIG. 6) using manual headspace GC-MS injection.

Manual headspace injection into GC-MS was successfully performed for all substrates with chain lengths of C11 to C6. Obtained product concentrations are summarized in Table 3. Conversion of 10 mM heptanoic acid allowed reliable formation of up to 1.3 mM 1-hexene without further optimization of the reaction conditions.

Example 6

Trapping, Derivatization and Quantification of 1-Butene and 1-Propene

Figure 7:
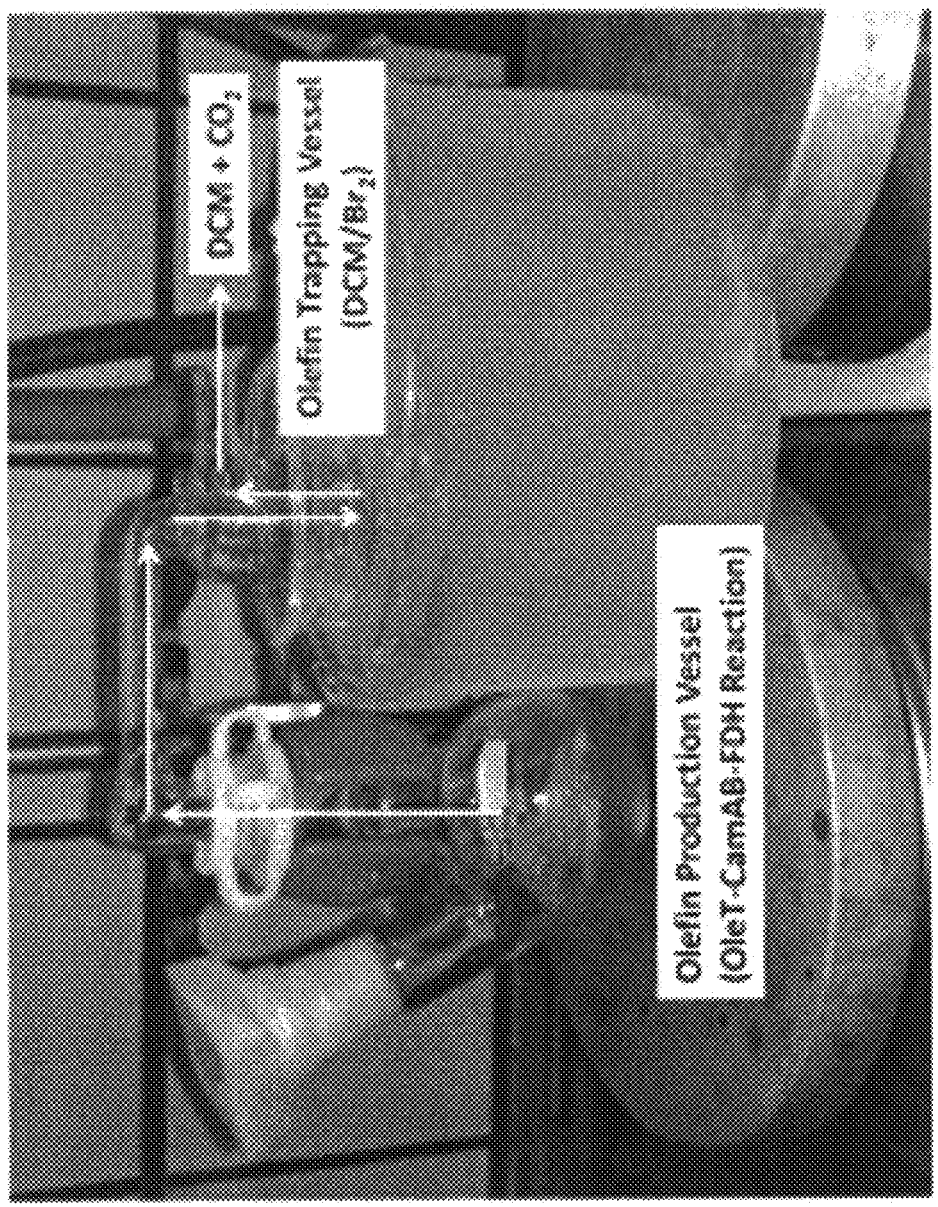
FIG. 7 is a picture of a novel reaction set up for trapping volatile α-olefins, such as 1-propene and 1-butene. A small impinger containing 10 ml of a 20 mM Br2/DCM solution was placed on top of the flask serving as sole gas outlet and trap for α-olefin products. The functionality of this system was successfully confirmed using an analytical standard of 1-heptene. The concept for derivatization and trapping of volatile α-olefins is shown in Scheme 2.
Figure 8A:
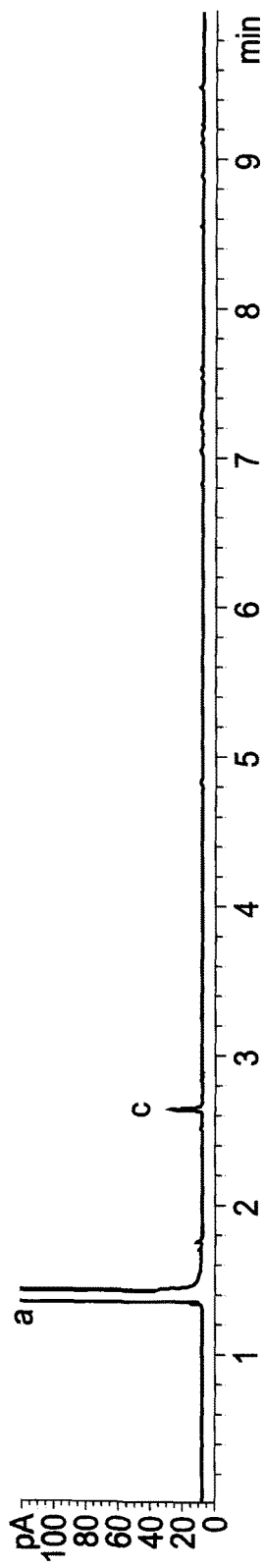
FIG. 8A-8D are GC-FID chromatograms from the production of 1-butene from valeric acid by the OleTCamAB-FDH cascade. 8A=impinger solution (DCM/Br2); 8B=content of the impinger solution after 24 h conversion of valeric acid by OleT-CamAB-FDH cascade; 8C=analytical standard of 1,2-dibromobutane; 8D=content of the impinger solution after 24 h conversion of valeric acid without OleT. a=solvent peak (DCM); b=1,2-dibromobutane; c=impurity from DCM solvent.
Figure 8B:
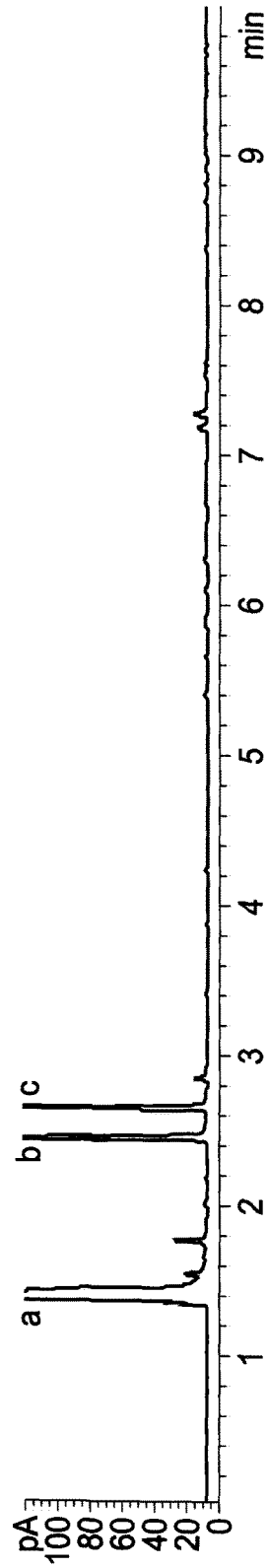
Figure 8C:
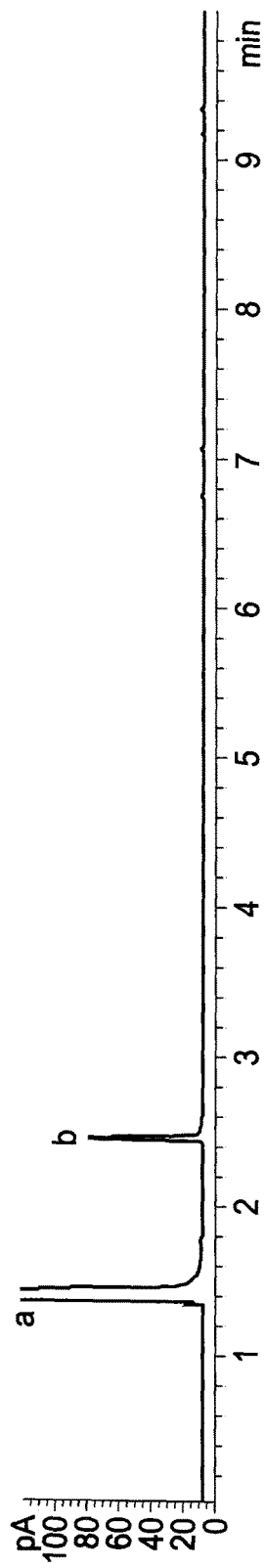
Figure 8D:
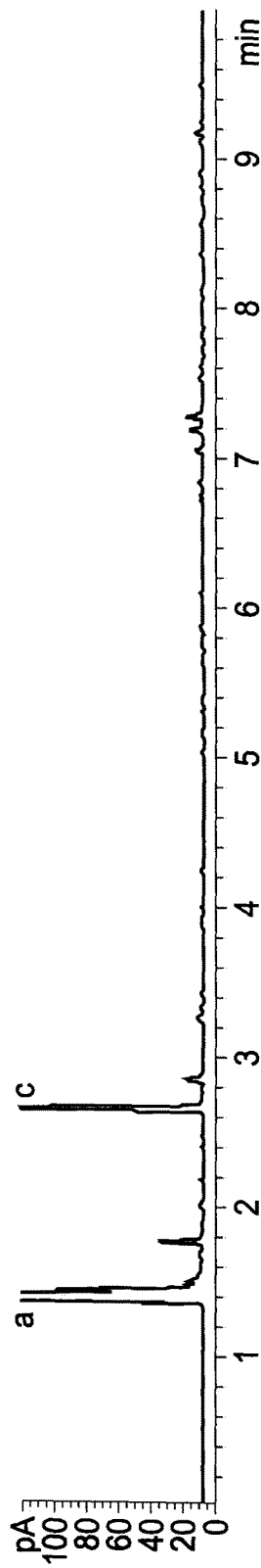
Figure 9A:
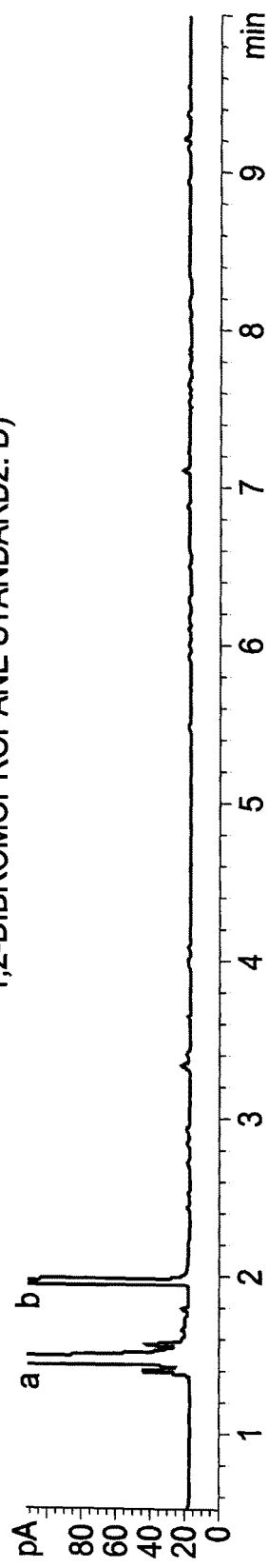
FIG. 9A-9D are GC-FID chromatograms from the production of 1-propene from valeric acid by the OleT-CamAB-FDH cascade. 9A=analytical standard of 1,2-dibromopropane; 9B=content of the impinger solution after 24 h conversion of valeric acid by OleT-CamAB-FDH cascade. 9C=content of the impinger solution after 24 h conversion of butyric acid by OleT-CamAB-FDH cascade; 9D=impinger solution (DCM/Br2); a=solvent peak (DCM); b=1,2-dibromopropane; c=1,2-dibromobutane; d=impurity from DCM solvent.
Figure 9B:
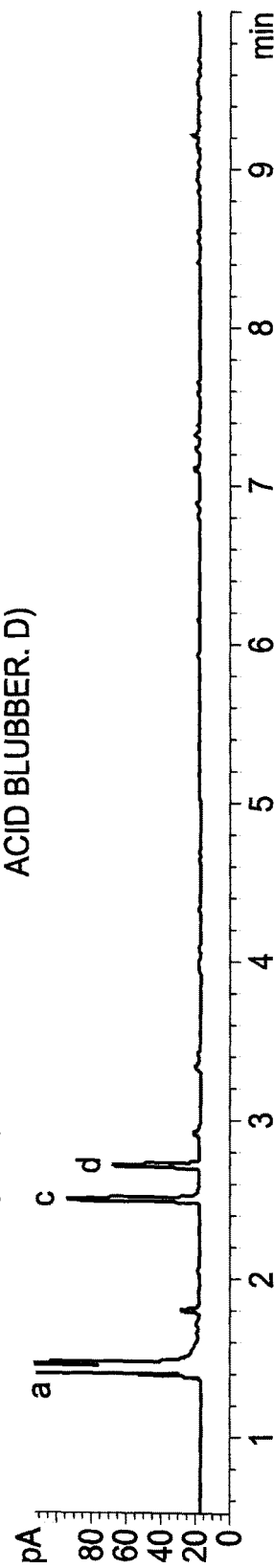
Figure 9C:
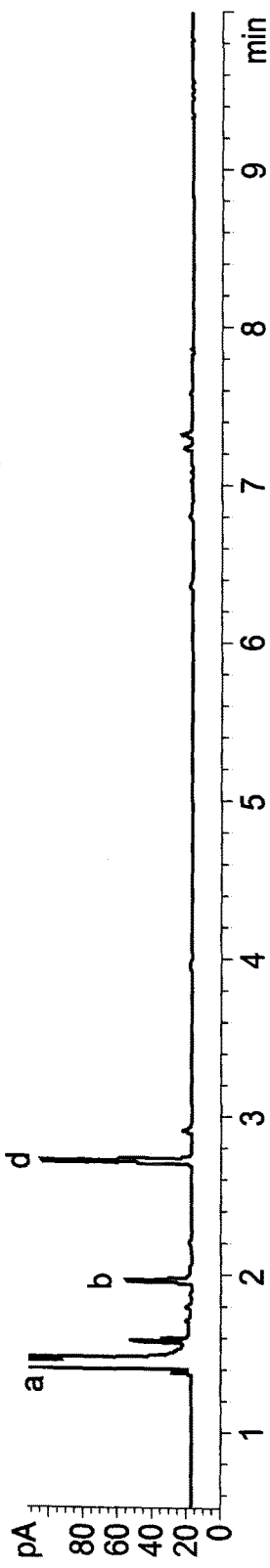
Figure 9D:
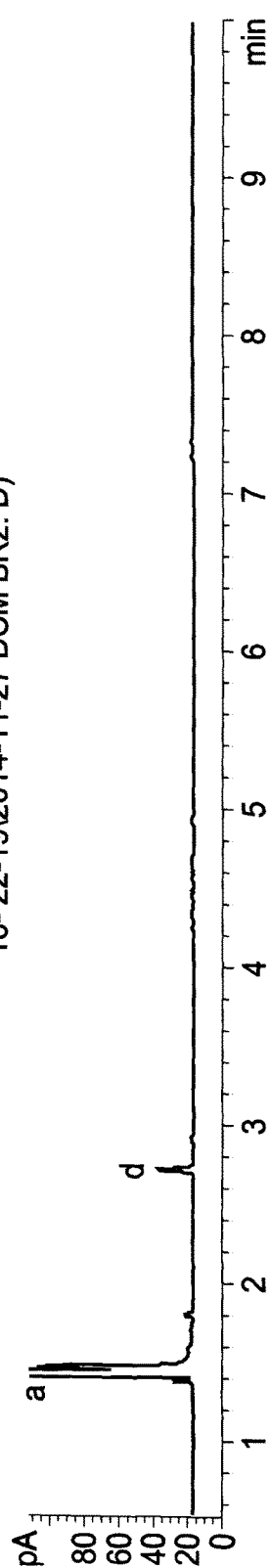

Production of 1-propene and 1-butene was initially confirmed using manual headspace GC-MS injection. Since the quantification of 1-propene and 1-butene using analytical standards was not feasible, a novel trapping/derivatization system for highly volatile short-chain α-olefins derived from biocatalytic reactions was designed. Thus, the established reaction set-up (see reaction conditions in Table 3) was upscaled to 10 ml (using 25 ml two-neck flasks) and the decarboxylation of butyric (C4) and valeric acid (C5) was performed in the set-up as shown in FIG. 7.

Scheme 2: Decarboxylation of butyric acid by the OleT-CamAB-FDH cascade followed by derivatization of the volatile 1-propene with Br2 in the impinger to give 1,2-dibromopropane as final reaction product.

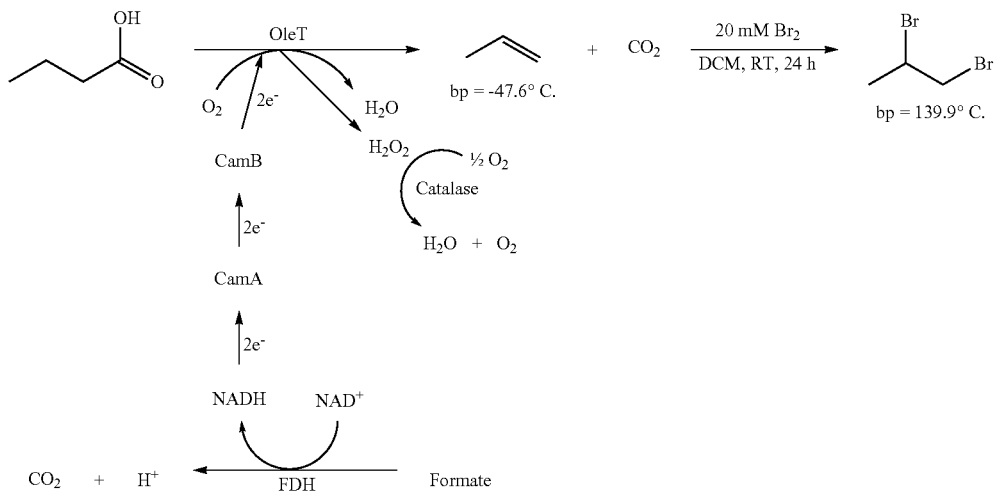

The obtained products were analyzed by GC-FID and GC-MS using analytical standards of 1,2-dibromobutane and 1,2-dibromopropane. Due to the (visible) gas exhaust ($CO_2$ production by OleT and FDH) and strong evaporation of DCM (~70% volume lost after 24 h), the residual volume in the impinger was determined to allow reliable product quantification. Calibration curves for 1,2-dibromobutane and 1,2-dibromopropane were prepared to allow quantification of produced 1-propene and 1-butene (not shown).

Further, the solution containing 1,2-dibromobutane was concentrated to 700 µl by dry air flow and analysed by 1H-NMR (FIG. 11) which serves as a further proof of 1-butene formation by OleT, Similarly, the solution containing 1,2-dibromopropane was concentrated to 700 µl by dry air flow and analysed by $^1$H-NMR (FIG. 16) which serves as a further proof of propene formation by OleT.

The analytical standard of 1,2-di-bromobutane is $^1$H NMR (300 MHz, $CDCl_3$) δ 4.23-4.09 (m, 1H), 3.87 (dd, J=10.2, 4.4 Hz, 1H), 3.66 (t, J=10.1 Hz, 1H), 2.22 (dqd, J=14.6, 7.3, 3.3 Hz, 1H), 1.97-1.74 (m, 1H), 1.09 (t, 7.2 Hz, 3H).

The analytical standard of 1,2-dibromopropane used was $^1$H NMR (300 MHz, $CDCl_3$) δ 4.34-4.20 (m, 1H), 3.87 (dt, J=10.1, 5.0 Hz, 1H), 3.58 (t, J=10.1 Hz, 1H), 1.85 (d, J=6.6 Hz, 3H).

Control reactions (CamAB-FDH cascade without OleT) were performed to confirm production of 1-propene and 1-butene only when the full cascade is re-constituted in the reaction vessel (FIGS. 8 and 9), The formation of 1,2-dibromobutane and 1,2-dibromopropane was also confirmed by GC-MS (not shown). With the novel trapping strategy, it was possible to identify and quantify both 1-propene and 1-butene. The conversion of 10 mM valeric acid led to the formation of 834 µM 1-butene, whereas 504 µM 1-propene were determined for conversion of 10 mM butyric acid. All reactions were performed at least in triplicate, and the corresponding α-olefins were the only reaction products detected in the impinger solution.

European patent application EPI 5156699 filed Feb. 26, 2015, is incorporated herein by reference.

Numerous modifications and variations on the present invention are possible in light of the above teachings. It is therefore to be understood that within the scope of the appended claims, the invention may be practiced otherwise than as specifically described herein.

REFERENCES

Belcher, J., et al., J Biol Chem, 2014. 289(10): p 6535-50.
Busto, E., et al., Chemistry, 2014. 20(35): p. 11225-8.
Carter J. L. L., ChemBioChem 2014, 15, 2710-2718
Dudek, et al., J. Biomol. Screen., 2013. 18(6): p. 678-687.
Fujishiro T, J Biol Chem 2011, 286:29941-29950.
Hannemman F., Biochimica et Biophysica Acta 1770 (2007) 330-344
Koga, H., et al., J Biochem, 1989. 106(5): p. 831-6.
Liu, Y., et al., Biotechnology for Biofuels, 2014, 7(28).
Malca. S. H., et al (2011) Biochimica et Biophysica Acta 1814 257-264
Matsunaga, I., et al., Archives of Biochemistry and Biophysics, 2001. 394(1): p. 45-53.
Matsunaga I, FEBS Lett 2002, 528:90-94.
Nazor, J., et al., Protein Eng Des Sel, 2008. 21(1): p. 29-35.
Roome, P. W., J Biol Chem, 1983. 258(4): p. 2593-8.
Rude, M. A., et al., Appl Environ Microbiol, 2011. 77(5): p. 1718-27.
Schallmey, A., et al., Appl Microbiol Biotechnol, 2011. 89(5): p. 1475-85.
Scheps D, Org. Biomol. Chem. 9: 6727-6733
Vrtis, J. M., et al., Chem Int Ed Engl, 2002. 41(17): p. 3257-9.

The invention claimed is:

1. A microbial cell capable of producing at least one terminal alkene from at least one $C_4$-$C_{10}$ fatty acid,
   wherein the microbial cell is genetically modified to comprise:
   at least one first genetic modification that increases the expression relative to the wild type cell of an enzyme ($E_1$) selected from the group consisting of $CYP_{SP\alpha}$ ($E_{1a}$), $CYP_{BSB}$ ($E_{1b}$) and OleT ($E_{1c}$); and
   at least one second genetic modification that increases the expression relative to the wild type cell of at least one NAD(P)+ oxidoreductase ($E_2$) and the corresponding mediator protein,
   wherein the NAD(P)+ oxidoreductase ($E_2$) and the corresponding mediator protein are:
   (a) ferredoxin reductase ($E_{2a}$) and ferredoxin; or
   (b) putidaredoxin reductase ($E_{2b}$) and putidaredoxin
   wherein $CYP_{SP\alpha}$ ($E_{1a}$), $CYP_{BSB}$ ($E_{1b}$) and OleT ($E_{1c}$) are members of the CYP152 peroxygenase family.

2. The microbial cell according to claim 1, wherein enzyme ($E_1$) is $CYP_{SP\alpha}$ ($E_{1a}$).

3. The microbial cell according to claim 1, wherein the enzyme ($E_1$) is OleT ($E_{1c}$) and has at least 60% sequence identity to SEQ ID NO:1.

4. The microbial cell according to claim 1, wherein the NAD(P)+ oxidoreductase ($E_2$) and the corresponding mediator protein are:
   (a) ferredoxin reductase ($E_{2a}$) and ferredoxin.

5. The microbial cell according to claim 1, wherein the NAD(P)+ oxidoreductase ($E_2$) has 60% sequence identity to SEQ ID NO:2 and the corresponding mediator protein has 60% sequence identity to SEQ ID NO:3.

6. The microbial cell according to claim 1, wherein the cell further comprises at least one third genetic modification that increases the expression relative to the wild type cell of at least one enzyme ($E_3$) capable of NAD(P)H regeneration.

7. The microbial cell according to claim 6, wherein the enzyme ($E_3$) is selected from the group consisting of glucose dehydrogenase, phosphite dehydrogenase and formate dehydrogenase.

8. The microbial cell according to claim 1, wherein the cell further comprises a reduced fatty acid degradation capacity relative to the wild type cell.

9. The microbial cell according to claim 8, wherein the fatty acid degradation capacity is reduced by deletion of a gene encoding an enzyme selected from the group consisting of fatty acid importer, fatty acid-CoA ligase, acyl-CoA dehydrogenase, 2,4-dienoyl-CoA reductase, enoyl-CoA hydratase and 3-ketoacyl-CoA thiolase.

10. The microbial cell according to claim 1, wherein the microbial cell is a prokaryotic or a lower eukaryotic cell.

11. A method of producing at least one terminal alkene, comprising:
contacting the microbial cell of claim 1 with the at least one $C_4$-$C_{10}$ fatty acid and collecting the alkene produced.

12. The cell according to claim 1, wherein the enzyme ($E_1$) is $CYP_{BSB}$ ($E_{1b}$).

13. The microbial cell according to claim 1, wherein the NAD(P)+ oxidoreductase ($E_2$) and the corresponding mediator protein are:
(b) putidaredoxin reductase ($E_{2b}$) and putidaredoxin.

14. The microbial cell according to claim 1,
wherein the enzyme ($E_1$) is OleT ($E_{1c}$) and has at least 60% sequence identity to SEQ ID NO:1, and
the NAD(P)+ oxidoreductase ($E_2$) has 60% sequence identity to SEQ ID NO:2 and the corresponding mediator protein has 60% sequence identity to SEQ ID NO:3.

15. The microbial cell according to claim 1,
wherein the enzyme ($E_1$) is OleT ($E_{1c}$) and has at least 95% sequence identity to SEQ ID NO:1, and
the NAD(P)+ oxidoreductase ($E_2$) has 95% sequence identity to SEQ ID NO:2 and the corresponding mediator protein has 95% sequence identity to SEQ ID NO:3.

16. The microbial cell according to claim 1, wherein the enzyme ($E_1$), the NAD(P)+ oxidoreductase ($E_2$) and the corresponding mediator protein are heterologous to the microbial cell.

17. The microbial cell according to claim 14, wherein the enzyme ($E_1$), the NAD(P)+ oxidoreductase ($E_2$) and the corresponding mediator protein are heterologous to the microbial cell.

18. The microbial cell according to claim 15, wherein the enzyme ($E_1$), the NAD(P)+ oxidoreductase ($E_2$) and the corresponding mediator protein are heterologous to the microbial cell.

19. The microbial cell according to claim 18, wherein the cell further comprises at least one third genetic modification that increases the expression relative to the wild type cell of at least one enzyme ($E_3$) capable of NAD(P)H regeneration.

20. The method according to claim 11, wherein the at least one $C_4$-$C_{10}$ fatty acid is at least one selected from the group consisting of isobutyric acid, butyric acid, isovaleric acid, and valeric acid.

* * * * *

SEQUENCE LISTING

<160> NUMBER OF SEQ ID NOS: 3

<210> SEQ ID NO 1
<211> LENGTH: 422
<212> TYPE: PRT
<213> ORGANISM: Micrococcus candicans ATCC 8456

<400> SEQUENCE: 1

```
Met Ala Thr Leu Lys Arg Asp Lys Gly Leu Asp Asn Thr Leu Lys Val
1               5                   10                  15

Leu Lys Gln Gly Tyr Leu Tyr Thr Thr Asn Gln Arg Asn Arg Leu Asn
            20                  25                  30

Thr Ser Val Phe Gln Thr Lys Ala Leu Gly Gly Lys Pro Phe Val Val
            35                  40                  45

Val Thr Gly Lys Glu Gly Ala Glu Met Phe Tyr Asn Asn Asp Val Val
        50                  55                  60

Gln Arg Glu Gly Met Leu Pro Lys Arg Ile Val Asn Thr Leu Phe Gly
65                  70                  75                  80

Lys Gly Ala Ile His Thr Val Asp Gly Lys Lys His Val Asp Arg Lys
                85                  90                  95

Ala Leu Phe Met Ser Leu Met Thr Glu Gly Asn Leu Asn Tyr Val Arg
            100                 105                 110

Glu Leu Thr Arg Thr Leu Trp His Ala Asn Thr Gln Arg Met Glu Ser
            115                 120                 125

Met Asp Glu Val Asn Ile Tyr Arg Glu Ser Ile Val Leu Leu Thr Lys
        130                 135                 140

Val Gly Thr Arg Trp Ala Gly Val Gln Ala Pro Pro Glu Asp Ile Glu
145                 150                 155                 160

Arg Ile Ala Thr Asp Met Asp Ile Met Ile Asp Ser Phe Arg Ala Leu
                165                 170                 175

Gly Gly Ala Phe Lys Gly Tyr Lys Ala Ser Lys Glu Ala Arg Arg Arg
            180                 185                 190

Val Glu Asp Trp Leu Glu Glu Gln Ile Ile Glu Thr Arg Lys Gly Asn
            195                 200                 205

Ile His Pro Pro Glu Gly Thr Ala Leu Tyr Glu Phe Ala His Trp Glu
        210                 215                 220

Asp Tyr Leu Gly Asn Pro Met Asp Ser Arg Thr Cys Ala Ile Asp Leu
225                 230                 235                 240

Met Asn Thr Phe Arg Pro Leu Ile Ala Ile Asn Arg Phe Val Ser Phe
                245                 250                 255

Gly Leu His Ala Met Asn Glu Asn Pro Ile Thr Arg Glu Lys Ile Lys
            260                 265                 270

Ser Glu Pro Asp Tyr Ala Tyr Lys Phe Ala Gln Glu Val Arg Arg Tyr
            275                 280                 285

Tyr Pro Phe Val Pro Phe Leu Pro Gly Lys Ala Lys Val Asp Ile Asp
        290                 295                 300

Phe Gln Gly Val Thr Ile Pro Ala Gly Val Gly Leu Ala Leu Asp Val
305                 310                 315                 320

Tyr Gly Thr Thr His Asp Glu Ser Leu Trp Asp Asp Pro Asn Glu Phe
                325                 330                 335

Arg Pro Glu Arg Phe Glu Thr Trp Asp Gly Ser Pro Phe Asp Leu Ile
            340                 345                 350

Pro Gln Gly Gly Gly Asp Tyr Trp Thr Asn His Arg Cys Ala Gly Glu
            355                 360                 365
```

```
Trp Ile Thr Val Ile Ile Met Glu Glu Thr Met Lys Tyr Phe Ala Glu
    370                 375                 380
Lys Ile Thr Tyr Asp Val Pro Glu Gln Asp Leu Glu Val Asp Leu Asn
385                 390                 395                 400
Ser Ile Pro Gly Tyr Val Lys Ser Gly Phe Val Ile Lys Asn Val Arg
                405                 410                 415
Glu Val Val Asp Arg Thr
                420

<210> SEQ ID NO 2
<211> LENGTH: 422
<212> TYPE: PRT
<213> ORGANISM: Pseudomonas putida

<400> SEQUENCE: 2

Met Asn Ala Asn Asp Asn Val Val Ile Val Gly Thr Gly Leu Ala Gly
1               5                   10                  15
Val Glu Val Ala Phe Gly Leu Arg Ala Ser Gly Trp Glu Gly Asn Ile
                20                  25                  30
Arg Leu Val Gly Asp Ala Thr Val Ile Pro His His Leu Pro Pro Leu
            35                  40                  45
Ser Lys Ala Tyr Leu Ala Gly Lys Ala Thr Ala Glu Ser Leu Tyr Leu
    50                  55                  60
Arg Thr Pro Asp Ala Tyr Ala Ala Gln Asn Ile Gln Leu Leu Gly Gly
65                  70                  75                  80
Thr Gln Val Thr Ala Ile Asn Arg Asp Arg Gln Gln Val Ile Leu Ser
                85                  90                  95
Asp Gly Arg Ala Leu Asp Tyr Asp Arg Leu Val Leu Ala Thr Gly Gly
                100                 105                 110
Arg Pro Arg Pro Leu Pro Val Ala Ser Gly Ala Val Gly Lys Ala Asn
            115                 120                 125
Asn Phe Arg Tyr Leu Arg Thr Leu Glu Asp Ala Glu Cys Ile Arg Arg
    130                 135                 140
Gln Leu Ile Ala Asp Asn Arg Leu Val Val Ile Gly Gly Gly Tyr Ile
145                 150                 155                 160
Gly Leu Glu Val Ala Ala Thr Ala Ile Lys Ala Asn Met His Val Thr
                165                 170                 175
Leu Leu Asp Thr Ala Ala Arg Val Leu Glu Arg Val Thr Ala Pro Pro
                180                 185                 190
Val Ser Ala Phe Tyr Glu His Leu His Arg Glu Ala Gly Val Asp Ile
            195                 200                 205
Arg Thr Gly Thr Gln Val Cys Gly Phe Glu Met Ser Thr Asp Gln Gln
    210                 215                 220
Lys Val Thr Ala Val Leu Cys Glu Asp Gly Thr Arg Leu Pro Ala Asp
225                 230                 235                 240
Leu Val Ile Ala Gly Ile Gly Leu Ile Pro Asn Cys Glu Leu Ala Ser
                245                 250                 255
Ala Ala Gly Leu Gln Val Asp Asn Gly Ile Val Ile Asn Glu His Met
                260                 265                 270
Gln Thr Ser Asp Pro Leu Ile Met Ala Val Gly Asp Cys Ala Arg Phe
            275                 280                 285
His Ser Gln Leu Tyr Asp Arg Trp Val Arg Ile Glu Ser Val Pro Asn
    290                 295                 300
Ala Leu Glu Gln Ala Arg Lys Ile Ala Ala Ile Leu Cys Gly Lys Val
305                 310                 315                 320
```

-continued

```
Pro Arg Asp Glu Ala Ala Pro Trp Phe Trp Ser Asp Gln Tyr Glu Ile
            325                 330                 335

Gly Leu Lys Met Val Gly Leu Ser Glu Gly Tyr Asp Arg Ile Ile Val
            340                 345                 350

Arg Gly Ser Leu Ala Gln Pro Asp Phe Ser Val Phe Tyr Leu Gln Gly
            355                 360                 365

Asp Arg Val Leu Ala Val Asp Thr Val Asn Arg Pro Val Glu Phe Asn
        370                 375                 380

Gln Ser Lys Gln Ile Ile Thr Asp Arg Leu Pro Val Glu Pro Asn Leu
385                 390                 395                 400

Leu Gly Asp Glu Ser Val Pro Leu Lys Glu Ile Ile Ala Ala Ala Lys
            405                 410                 415

Ala Glu Leu Ser Ser Ala
            420

<210> SEQ ID NO 3
<211> LENGTH: 107
<212> TYPE: PRT
<213> ORGANISM: Pseudomonas putida

<400> SEQUENCE: 3

Met Ser Lys Val Val Tyr Val Ser His Asp Gly Thr Arg Arg Glu Leu
1               5                   10                  15

Asp Val Ala Asp Gly Val Ser Leu Met Gln Ala Ala Val Ser Asn Gly
            20                  25                  30

Ile Tyr Asp Ile Val Gly Asp Cys Gly Gly Ser Ala Ser Cys Ala Thr
        35                  40                  45

Cys His Val Tyr Val Asn Glu Ala Phe Thr Asp Lys Val Pro Ala Ala
        50                  55                  60

Asn Glu Arg Glu Ile Gly Met Leu Glu Cys Val Thr Ala Glu Leu Lys
65                  70                  75                  80

Pro Asn Ser Arg Leu Cys Cys Gln Ile Ile Met Thr Pro Glu Leu Asp
            85                  90                  95

Gly Ile Val Val Asp Val Pro Asp Arg Gln Trp
            100                 105
```